(12) United States Patent
Tavernier et al.

(10) Patent No.: US 7,575,878 B2
(45) Date of Patent: Aug. 18, 2009

(54) METHODS OF INHIBITING LEPTIN-INDUCED SIGNALING WITH FIBRONECTIN III DOMAIN ANTIBODIES

(75) Inventors: Jan Tavernier, Balegem (BE); Lennart Zabeau, Gent (BE)

(73) Assignees: VIB vzw, Zwijnaarde (BE); Universiteit Gent, Gent (BE)

( * ) Notice: Subject to any disclaimer, the term of this patent is extended or adjusted under 35 U.S.C. 154(b) by 0 days.

(21) Appl. No.: 11/791,264

(22) PCT Filed: Nov. 16, 2005

(86) PCT No.: PCT/EP2005/056022

§ 371 (c)(1),
(2), (4) Date: Jun. 20, 2007

(87) PCT Pub. No.: WO2006/053883

PCT Pub. Date: May 26, 2006

(65) Prior Publication Data

US 2007/0292434 A1     Dec. 20, 2007

(30) Foreign Application Priority Data

Nov. 18, 2004  (EP) ................................. 04105864

(51) Int. Cl.
*G01N 33/53* (2006.01)
*C07K 16/00* (2006.01)
(52) U.S. Cl. ..................... 435/7.1; 435/7.2; 530/387.1
(58) Field of Classification Search .................. None
See application file for complete search history.

(56) References Cited

U.S. PATENT DOCUMENTS

| | | | |
|---|---|---|---|
| 5,521,066 A | 5/1996 | Menzel et al. | |
| 5,686,281 A | 11/1997 | Roberts | |
| 5,716,622 A | 2/1998 | Darnell et al. | |
| 5,744,314 A | 4/1998 | Menzel et al. | |
| 5,776,689 A | 7/1998 | Karin et al. | |
| 5,843,697 A | 12/1998 | Pestka et al. | |
| 5,885,779 A | 3/1999 | Sadowski et al. | |
| 5,972,621 A | 10/1999 | Tartaglia et al. | |
| 6,001,816 A | 12/1999 | Morsy et al. | |
| 6,270,964 B1 | 8/2001 | Michnick et al. | |
| 6,294,330 B1 | 9/2001 | Michnick et al. | |
| 6,303,319 B1 | 10/2001 | Rickles | |
| 6,342,345 B1 | 1/2002 | Blau et al. | |
| 6,380,363 B1* | 4/2002 | Tartaglia et al. | ........ 530/388.22 |
| 6,734,006 B2 | 5/2004 | Xiao et al. | |
| 2001/0023062 A1 | 9/2001 | Ostade et al. | |
| 2004/0202652 A1* | 10/2004 | Karsenty et al. | ......... 424/133.1 |

FOREIGN PATENT DOCUMENTS

| | | |
|---|---|---|
| EP | 0 646 644 A2 | 4/1995 |
| WO | WO 96/05309 | 2/1996 |
| WO | WO 97/00319 | 1/1997 |
| WO | WO 97/20933 | 6/1997 |
| WO | WO97/26335 | 7/1997 |
| WO | WO 97/31113 | 8/1997 |
| WO | WO 97/46585 | 12/1997 |
| WO | WO 98/02542 | 1/1998 |
| WO | WO 98/12224 | 3/1998 |
| WO | WO 98/20158 | 5/1998 |
| WO | WO 98/34120 | 8/1998 |
| WO | WO 98/44350 | 10/1998 |
| WO | WO 99/03974 | 1/1999 |
| WO | WO 99/40946 A2 | 8/1999 |
| WO | WO 00/06722 | 2/2000 |
| WO | WO 00 07014 | 2/2000 |
| WO | WO 00/07038 | 2/2000 |
| WO | WO 02/40543 A1 | 5/2002 |
| WO | WO 02/062833 A2 | 8/2002 |

OTHER PUBLICATIONS

Banks et al., Activation of Downstream Signals by the Long Form of the Leptin Receptor, Journal of Biological Chemistry, May 12, 2000, pp. 14563-14572, vol. 275, No. 19, U.S.A.

Baumann et al., Proc. Natl. Acad. Sci. USA, 1996, pp. 8374-8378, vol. 93.

Beattie, et al., Obesity and Hyperleptinemia in Metallothionein (-I and -II) Null Mice, Proceedings of the National Academy of Sciences of USA, Jan. 1998, pp. 358-363, vol. 95.

Bjorbaek et al., Identification of SOCS-3 as a Potential Mediator of Central Leptin Resistance, Molecular Cell, Mar. 1998, pp. 619-625, vol. 1, No. 4.

Bjorbaek et al., The Role of SOCS-3 in Leptin Signaling and Leptin Resistance, The Journal of Biological Chemistry, Oct. 15, 1999, pp. 30059-30065, vol. 274, No. 42.

Bonnefoy-Berard et al., "Vav: Function and Regulation in Hematopoietic Cell Signaling," 14 Stem Cells 250-68 (1996).

Campfield et al., Science, 1998, pp. 1383-1389, vol. 280.

Carpenter et al., Proc Natl Acad Sci USA, 1998, pp. 6061-6066, vol. 95.

Colas et al., The impact of two-hybrid and related methods on biotechnology, Trends in Biotechnology, Aug. 1998, pp. 355-363, vol. 16.

Daly et al., Recognition of human colon cancer by T cells transduced with a chimeric receptor gene, Cancer Gene Therapy, 2000, pp. 284-291, vol. 7, No. 2.

David et al., J. Biol. Chem. 1996, pp. 4585-4588, vol. 271.

Dusetti et al., Structural organization of the gene encoding the rat pancreatitis-associated protein, Jul. 5, 1993, pp. 14470-14475, vol. 268.

(Continued)

*Primary Examiner*—Robert Landsman
*Assistant Examiner*—Gyan Chandra
(74) *Attorney, Agent, or Firm*—TraskBritt

(57) ABSTRACT

The invention relates to a new type of leptin receptor antagonist, which is able to prevent leptin signaling without preventing the binding of leptin to the leptin binding domain. More specifically, the invention relates to the use of a part of the leptin receptor to prevent the leptin-dependent activation of the receptor, and by this the leptin-induced signaling.

3 Claims, 10 Drawing Sheets

OTHER PUBLICATIONS

Dusetti et al., The pancreatitis-associated protein I promoter allows targeting to the pancreas of a foreign gene whose expression is up-regulated during pancreatic inflammation, Feb 28, 1997, pp. 5800-5804.

Eyckerman et al., Analysis of Tyr to Phe and fa/fa leptin receptor mutations in the PC12 cell line, Eur. Cytokine Netw, Dec. 1999, pp. 549-556, vol. 10, No. 4.

Eyckerman et al., Design and application of a cytokine-receptor-based interaction trap, Nature Cell Biology, Dec. 2001, pp. 1114-1119, vol. 3, EBSCO Publishing.

Fields et al., The two-hybrid system: an assay for protein-protein interactions, Trends in Genetics, Aug. 1994, pp. 286-292, vol. 10, No. 8.

Ghilardi et al., Proc. Natl. Acad. Sci. USA, 1996, pp. 6231-6235, vol. 93.

Gisselbrecht, Sylvie, The CIS/SOCS proteins: a family of cytokine-inducible regulators of signaling, 10(4) European Cytokine Network 463-470 (Dec. 1999), retrieved from <URL:http://www.john-libbey-eurotest.fr/articles/ccn/10/4/463-70/> Jul. 12, 2001.

Grasso et al., Endocrinol, 1997, pp. 1413-1418, vol. 138.

Ihle et al., Jaks and Stats in signaling by the cytokine receptor superfamily, Trends Genet., Feb. 1995, pp. 69-74, vol. 11, No. 2.

Iyengar, FASEB J., 1993, pp. 768-775, vol. 7.

Lee et al., Abnormal splicing of the leptin receptor in diabetic mice, Nature, Feb. 15, 1996, pp. 632-635, vol. 379.

Medici et al., The EMBO Journal, 1997, pp. 7241-7249, vol. 16, No. 24.

Mercer et al., Localization of leptin receptor mRNA and the long form splice variant (Ob-Rb) in mouse hypothalamus and adjacent brain regions by in situ hybridization, FEBS Letters, 1996, pp. 113-116, vol. 387.

Montoye et al., Analysis of leptin signalling in hematopoietic cells using an adapted MAPPIT strategy, FEBS Letters, 2006, pp. 3301-3307, vol. 580.

Montoye et al., In Press, A systematic scan of interactions with tyrosine motifs in the erythropoietin receptor using a mammalian two-hybrid approach.

Nakashima et al., FEBS, 1997, pp. 79-82, vol. 403.

Ngo et al., The Protein Folding Problem and Tertiary Structure Prediction, Chapter 14: Computational Complexity Protein Structure Prediction, and the Levinthal Paradox, Mar. 2, 1994, pp. 492-495.

Okuda et al., Ann N Y Acad Sci., 1999, pp. 305-312, vol. 872.

Osborne et al., The Yeast Tribrid System—Genetic Detectiion of trans-phosphorylated ITAM-SH2-Interactions, Biotechnology, Dec. 13, 1995, pp. 1474-1478, vol. 13.

Overton et al., Current Biology, 2000, pp. 341-344, vol. 10, No. 6.

Ray et al., J. Clin. Invest. 1996, pp. 1852-1859, vol. 97.

Rohner-Jearnrenaud et al., The New Eng. J. Med., 1996, pp. 324-325, vol 334.

Saitoh et al., Identification of Important Regions in the Cytoplasmic Justamembrane Domain of Type I Receptor That Separate Signaling Pathways of Transforming Growth Factor-beta, The Journal of Biological Chemistry, Feb. 2, 1996, pp. 2769-2775, vol. 271, No. 5.

Shores et al., Curr Opin Immunol., 1997, pp. 380-389, vol. 9, No. 3.

Stoffel et al., Permissive role of thrombopoietin and granulocyte colony-stimulating factor receptors in hematopoietic cell fate decision in vivo, Proc. Natl. Acad. Sci. Jan. 1999, pp. 698-702, vol. 96.

Tartaglia et al., Identification and Expression Cloning of a Leptin Receptor, OB-R, Cell, Dec. 29, 1995, pp. 1263-1271, vol. 83.

Vaisse et al., Leptin Activation of Stat3 in the Hypothalamus of Wild-Type and ob/ob Mice but not db/db Mice, Nature Genetics, Sep. 14, 1996, pp. 95-97, vol. 14.

Verploegen et al., FEBS Letters, 1997, pp. 237-240, vol. 405.

Waelput et al., Analysis of Signal Transduction via the Leptin Receptor, International Journal of Obesity, Aug. 1998, pp. S99, vol. 22, No. Suppl. 3.

Wells, Additivity of Mutational Effects in Proteins, Biochemistry, Sep. 18, 1990, pp. 8509-8517, vol. 29, No. 37.

Zabeau et al., The ins and outs of leptin receptor activation, FEBS Letters, 2003, pp. 45-50, vol. 546.

Fazeli et al., Identification of a monoclonal antibody against the leptin receptor that acts as an antagonist and blocks human monocyte and T cell activation, Journal of Immunological Methods, 2006, pp. 190-200, vol. 312.

* cited by examiner

FIGURES
Fig. 1:
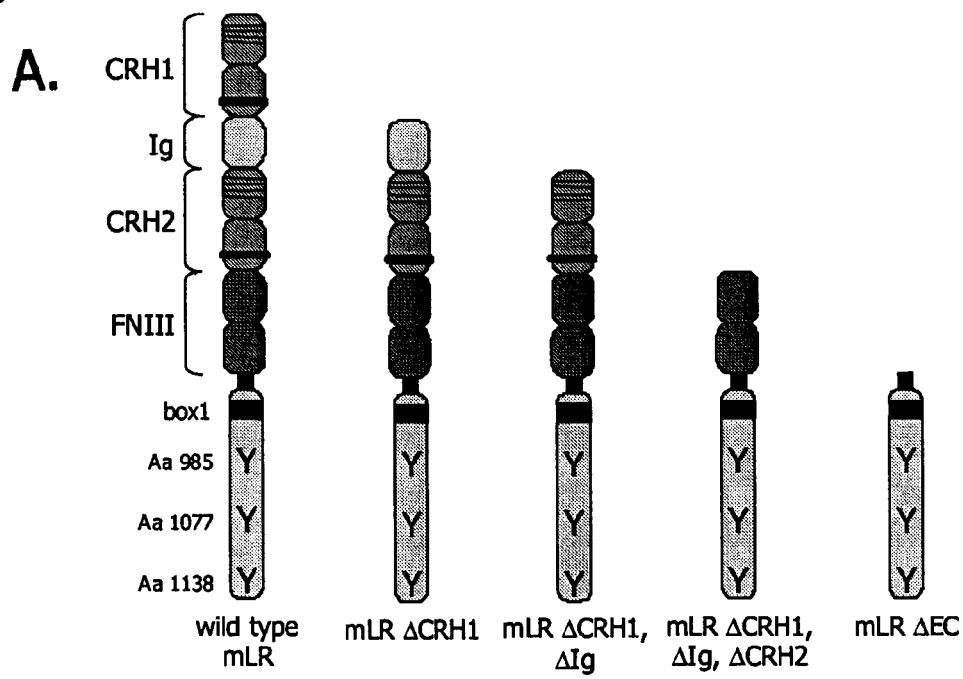
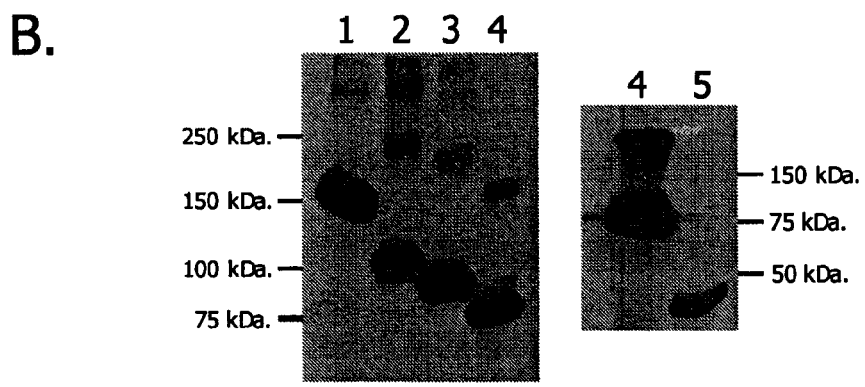
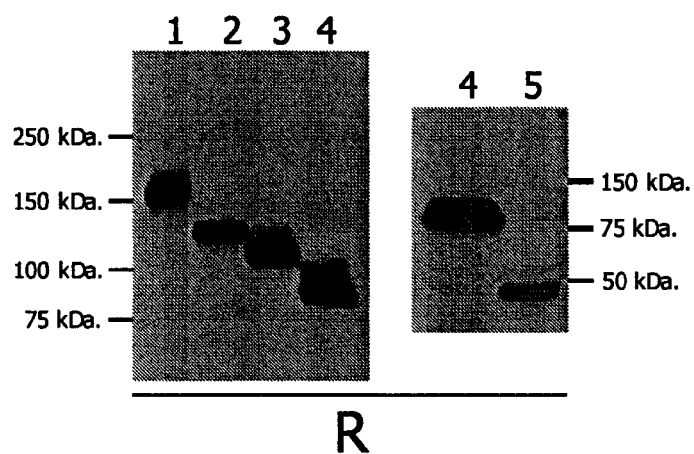

Fig. 9:
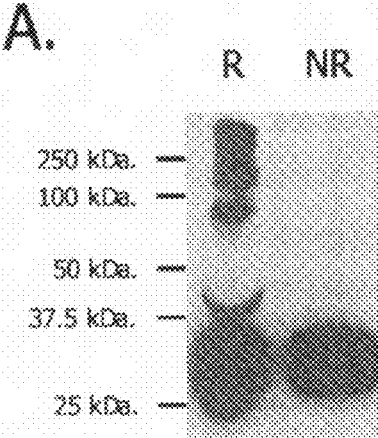
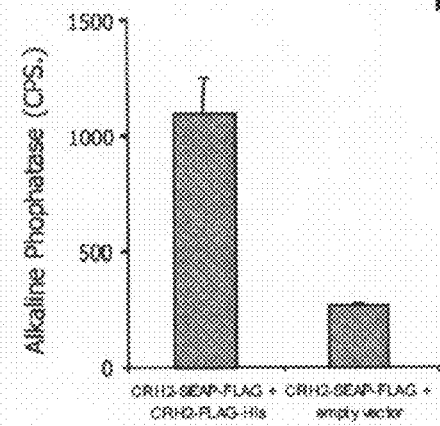
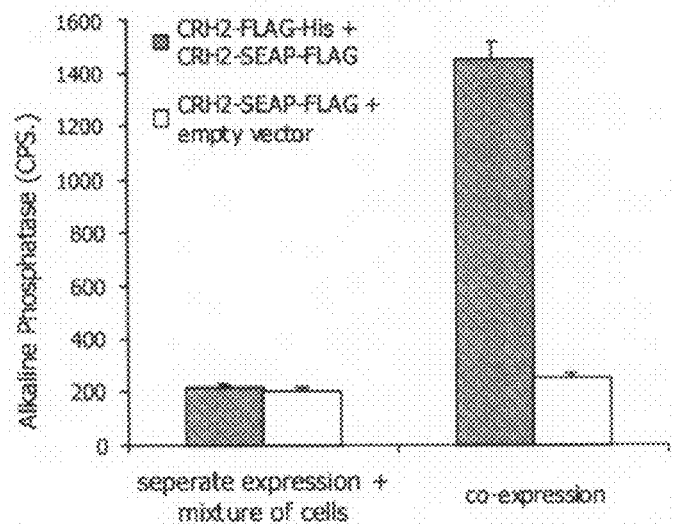
Fig. 10:
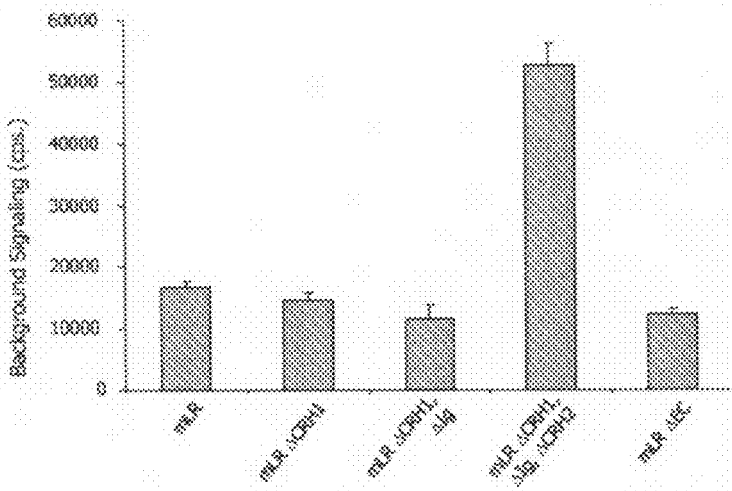

METHODS OF INHIBITING LEPTIN-INDUCED SIGNALING WITH FIBRONECTIN III DOMAIN ANTIBODIES

CROSS-REFERENCE TO RELATED APPLICATIONS

This is a national phase entry under 35 U.S.C. § 371 of International Patent Application PCT/EP2005/056022, filed Nov. 16, 2005, published in English as International Patent Publication WO 2006/053883 A1 on May 26, 2006, which claims the benefit under 35 U.S.C. § 119 of European Patent Application Serial No. 04105864.5, filed Nov. 18, 2004.

TECHNICAL FIELD

The invention relates to a new type of leptin receptor antagonist, which is able to prevent leptin signaling without preventing the binding of leptin to the leptin-binding domain. More specifically, the invention relates to the use of a part of the leptin receptor to prevent the leptin-dependent activation of the receptor and, by this, the leptin-induced signaling.

BACKGROUND

Leptin, the product of the ob gene, is a key player in energy homeostasis and body weight control. It is a 16-kDa circulating protein with a structure resembling 4-α-helical bundle cytokines (Madej et al., 1995). It is mainly secreted by adipose cells, and the circulating level of this hormone strongly correlates with white adipose tissue mass. Leptin regulates energy expenditure and food intake by activating its receptor in certain nuclei of the hypothalamus (Halaas et al., 1995; Campfield et al., 1995; Pelleymounter et al., 1995). Loss-of-function mutations within the genes for leptin (Montague et al., 1997), or for its receptor (Lee et al., 1997; Chen et al., 1996; Clement et al., 1998) cause complex syndromes characterized by morbid obesity, hyperglycemia, hyperinsulinemia, and reduced fertility. Numerous data suggest that leptin also has direct effects on tissues outside the brain, which may help explain its role on basal metabolism, reproduction, hematopoiesis and regulation of the immune response (Chebab et al., 2002; Baile et al., 2000; Fantuzzi and Faggioni, 2000; Matarese et al., 2002).

The leptin receptor (LR) is composed of a single subunit, encoded by the db gene (Lee et al., 1996; Chen et al., 1996; Tartaglia et al., 1995; Cioffi et al., 1996), and which is a member of the class I cytokine receptor family. It contains two so-called CRH modules, which are formed by two barrel-like domains, each approximately 100 amino acids (aa) in length, and which resemble the fibronectin type III (FN III) and immunoglobulin (Ig) folds. Two conserved disulfide bridges are found in the N-terminal sub-domain, while a WSXWS (SEQ ID NO: 22) motif is characteristic for the C-terminal sub-domain. Both LR CRH modules are separated by an Ig-like domain, and are followed by two membrane proximal FN III domains (FIG. 1). Using a panel of deletion and substitution mutants, Fong and co-workers (1998) showed that the membrane proximal CRH domain is necessary and sufficient for leptin binding, and that the two FN III domains are not involved in ligand binding. Thus far, six isoforms of the LR generated by alternative mRNA splicing have been recognized and termed LRa through LRf. The LR long form (LRlo, or LRb) has an intracellular chain length of 302 aa, and is the only isoform capable of efficient signaling. It is this LRlo isoform that is primarily expressed in specific nuclei of the hypothalamus (Mercer et al., 1996; Fei et al., 1997; Schwartz et al., 1996), but expression at lower levels in other cell-types has also been observed (Hoggard et al., 1997; Ghilardi et al., 1996; Dyer et al., 1997). A second isoform, LRa, is a variant lacking most of the cytosolic domain. This LR short form (LRsh) is much more widely expressed, often at higher levels compared to LRlo, e.g., in the choroid plexus, kidney, lung, and liver (Tartaglia, 1997).

As activation of the leptin receptor by binding of leptin plays a role in several physiological processes, several variant and mutant forms of leptin and leptin receptors have been described that can be used to modulate leptin signaling. WO9605309 discloses, amongst others, antibodies against leptin. WO9812224 describes the use of fragments, derived from leptin, as leptin antagonist, especially for treating type II diabetes. The use of leptin antagonists is known to the person skilled in the art and includes, but is not limited to, diseases and conditions associated with obesity such as atherosclerosis, hypertension and type II diabetes, the modulation of body weight, the modulation of inflammation, the modulation of immune responses and autoimmune diseases.

Most modulators are based on preventing the interaction of leptin with the membrane-bound leptin receptor. However, it would be interesting to block leptin-induced signaling without blocking the interaction of leptin with the soluble receptor, as this would increase the flexibility of the regulation.

Surprisingly, we found that binding of a compound to non-leptin-binding domains of the extracellular part of the leptin receptor can block the leptin-induced signaling without blocking the leptin binding. This inhibitory effect is realized by disturbing the leptin-induced clustering of the receptor and the consequent signaling. Indeed, inhibiting the fibronectin III-fibronectin III domain interaction in the leptin receptor can block the leptin-induced signaling. This inhibition can be realized by a soluble fibronectin III domain of the leptin receptor and/or by a fibronectin III domain binding antibody. Alternatively, an antibody directed against the Ig-like domain of the leptin receptor may be used.

DISCLOSURE OF THE INVENTION

A first aspect of the invention is the use of an extracellular domain of the leptin receptor to inhibit leptin-induced signaling, whereby the extracellular domain itself is not binding leptin. Preferably, the leptin receptor is a human leptin receptor. One preferred embodiment is the use of a fibronectin III domain, which does not bind leptin itself, to inhibit leptin-induced activation and signaling of the leptin receptor. Preferably, the fibronectin III domain is derived from the leptin receptor. Even more preferably, the fibronectin III domain comprises SEQ ID NO:1 and/or SEQ ID NO:2. More preferably, the fibronectin III domain comprises SEQ ID NO:3. Most preferably, the fibronectin III domain consists of SEQ ID NO:3. Inhibition by using the fibronectin domain preferably does not prevent the binding of leptin to the leptin receptor. This means that, even in the presence of leptin bound to the receptor, the leptin-induced signaling is blocked. However, it is clear for the person skilled in the art that the inhibition of the leptin signaling may be carried out, both at the level of the fibronectin III domain and at the level of the ligand binding, resulting in an increased inhibition. This double inhibition may be carried out by a mixture of at least two compounds, or it may be carried out by one compound obtained by fusing a fibronectin III binding domain to a domain that prevents the binding of leptin to the leptin receptor, with the proviso that this fused compound is not a soluble leptin receptor.

The use of a fibronectin III domain, as mentioned here, may be the use as a target sequence for inhibition, or it may be the use as an inhibitor itself. Indeed, as fibronectin III is involved in the activation of the leptin receptor by a fibronectin III-fibronectin III interaction, a soluble fibronectin III domain will bind to the fibronectin III domain of the receptor and influence the conformation and of the receptor cluster and the subsequent activation of the receptor.

Therefore, another aspect of the invention is the use of a soluble fibronectin III domain to inhibit leptin-induced signaling. Alternatively, instead of a soluble fibronectin III domain, any compound that binds to the fibronectin III domain of the leptin receptor, or prevents the fibronectin III-fibronectin III domain interaction of the leptin receptor, can be used. In one preferred embodiment, the compound prevents the disulphide bridge formation at position cys672 and/or cys751. Even more preferably, it prevents the disulphide bridge formation at position cys672. A "compound" as used herein means any chemical of biological compound, including simple or complex organic and inorganic molecules, peptides, peptido-mimetics, proteins, antibodies, carbohydrates, nucleic acids or derivatives thereof. Preferably, the compound is an antibody. The antibody can be any antibody, such as a polyclonal antibody, a monoclonal antibody or a single chain antibody. Preferably, the antibody is a camelid antibody, or a derivative thereof, such as a nanobody (VHH).

Another preferred embodiment is the use of the Ig-like domain of the leptin receptor, preferably the use of the Ig-like domain of a human leptin receptor (amino acid residue 329-427 of GenPept gi: 1589772), which does not bind leptin itself, to inhibit leptin-induced activation and signaling of the leptin receptor. Preferably, the Ig-like domain is derived from the leptin receptor. Inhibition by using the Ig-like domain preferably does not prevent the binding of leptin to the leptin receptor. This means that, even in-presence of leptin bound to the receptor, the leptin-induced signaling is blocked. Preferably, the use of the Ig-like domain is the use as target for binding of an Ig-domain binding compound. Even more preferably, the Ig-domain binding compound is an anti-Ig-like domain antibody. It is clear for the person skilled in the art that the inhibition may be increased by combining the inhibition at the Ig-like domain level by an inhibition at the fibronectin III domain level and/or with an inhibition at the leptin binding level. This multiple inhibition may be carried out by a mixture of compounds, or it may be carried by fusing the Ig-like binding compound to a compound that prevents the binding of leptin to the leptin receptor and/or a compound that binds to the fibronectin III domain, with the proviso that this fused compound is not a soluble leptin receptor.

Another aspect of the invention is an anti-fibronectin III domain antibody capable of blocking leptin signaling without inhibiting leptin binding. Still another aspect of the invention is an anti-Ig-like antibody capable of blocking leptin signaling without inhibiting leptin binding. Preferably, the antibodies are directed against extracellular domains of the leptin receptor. Even more preferably, the antibodies are camelid antibodies, or derivatives thereof, such as nanobodies. "Capable of blocking leptin signaling" as used herein means that the antibody is blocking leptin-induced receptor activation and signaling when it binds to its target domain.

Another aspect of the invention is a method to inhibit leptin-induced signaling by using an extracellular domain of the leptin receptor, which does not bind leptin itself. Preferably, the extracellular domain is selected from the group consisting of the fibronectin III domain of the leptin receptor and the Ig-like domain of the leptin receptor. One preferred embodiment is the method, whereby the fibronectin III domain of the leptin receptor is used as target for fibronectin III binding compounds. Preferably, the compound is a fibronectin III domain binding antibody. Another preferred embodiment is the method, whereby a polypeptide comprising the soluble fibronectin III domain is used as a fibronectin III binding compound. Preferably, the polypeptide consists of a soluble fibronectin III domain. Still another preferred embodiment is the method, whereby the Ig-like domain of the leptin receptor is used as target for Ig-like domain binding compounds. Preferably, the compound is an Ig-like domain binding antibody.

BRIEF DESCRIPTION OF THE DRAWINGS

FIG. 1: Expression and ligand-independent clustering of LR deletion variants:

Panel A: Schematic representation of the wild-type mLR and deletion variants thereof. The domain structure of the extracellular part is outlined, as well as determinants for signaling in the cytoplasmic tail. CRH: cytokine receptor homology; Ig: immunoglobulin; FNIII: fibronectin type III; Aa: amino acid; and Y: tyrosine residue. See text for details.

Panel B: COS-1 cells were transfected with plasmids encoding different LR deletion variants: full length (1); mLR ΔCRH1 (2); mLR ΔCRH1, ΔIg (3); mLR ΔCRH1, ΔIg, ΔCRH2 (4); and mLR ΔEC (5). Cells were lyzed in either a reducing, β-mercapto-ethanol-containing loading buffer (R), or in a non-reducing loading buffer (NR). Protein complexes were separated with SDS-PAGE, blotted onto a nitrocellulose membrane and revealed with an anti-FLAG antibody.

Figure 2:
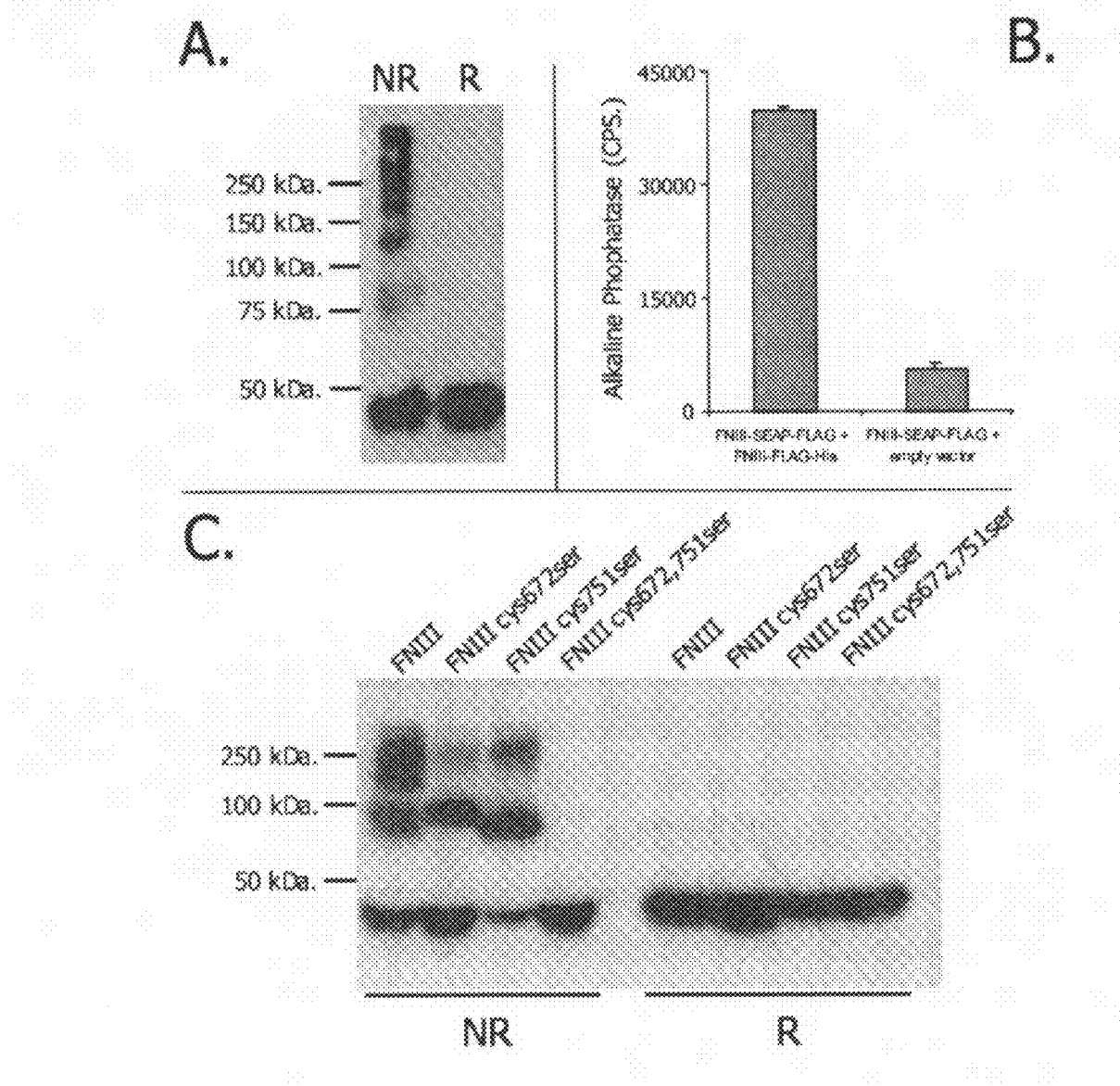

FIG. 2: FNIII clustering in solution:

Panel A: The plasmid encoding FNIII-FLAG-His was transfected in COS-1 cells. Supernatant was subjected to Western blot analysis under reducing (R) or non-reducing (NR) conditions with an anti-FLAG antibody.

Panel B: Hek293T cells were co-transfected with cDNA encoding FNIII-SEAP-FLAG in combination with FNIII-FLAG-His or with empty vector (as indicated). Three days after transfection, supernatants were collected and subjected to precipitation with the $Ni^{2+}$ metal affinity resin. After three successive washes and subsequent elution, co-precipitated alkaline phosphatase activity was measured using the CSPD substrate. Bars shown represent mean values and S.D. values of triplicate measurements.

Panel C: FNIII-FLAG-His and mutants thereof (as indicated) were transiently expressed and analyzed as described above.

Figure 3:
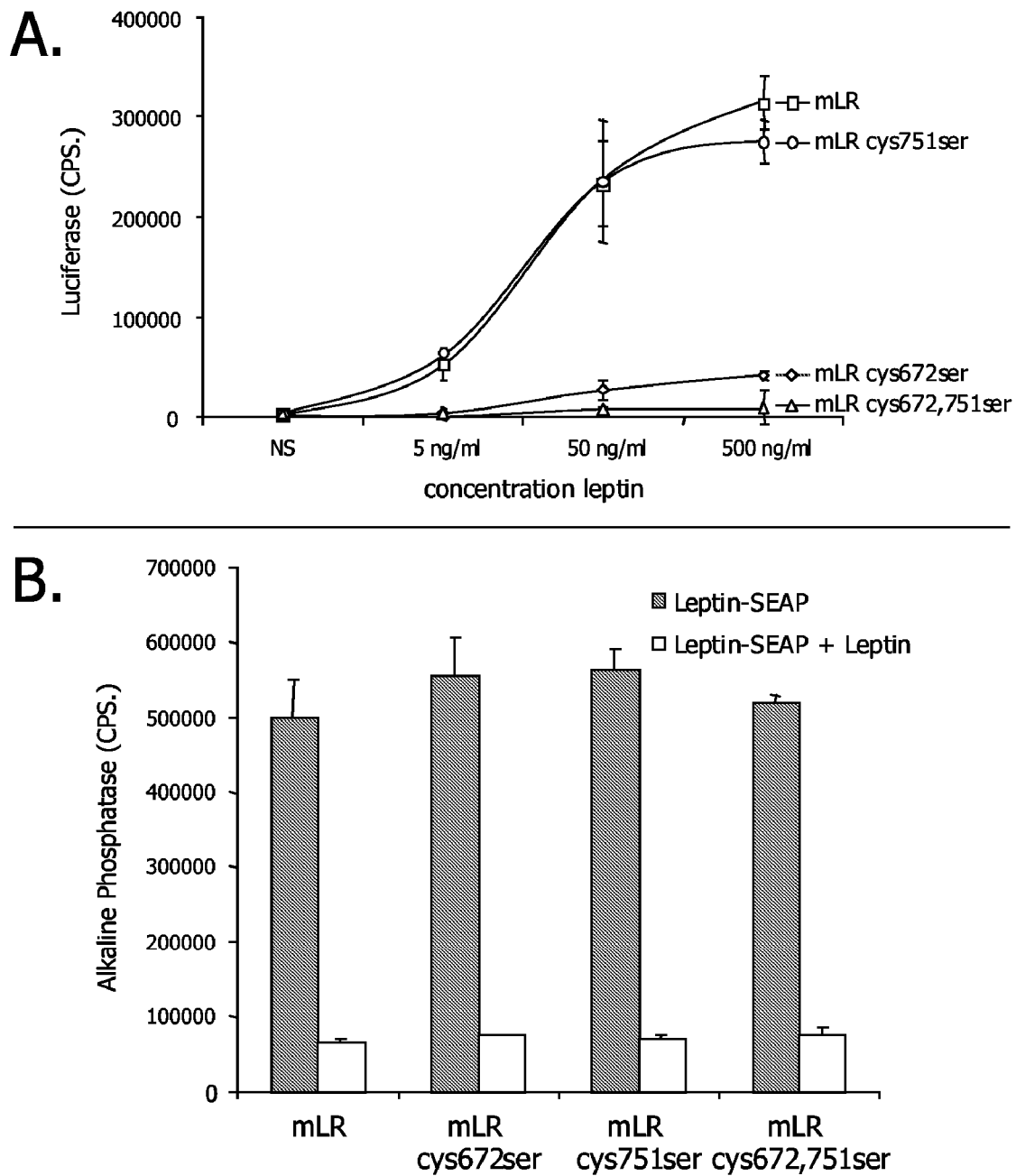

FIG. 3: Role of cys672 and cys751 in receptor activation, expression and ligand binding:

Panel A: pMET7 expression plasmids with mLR, mLR cys672ser, mLR cys751ser, or mLR cys672,751ser were transfected in Hek293T cells. The pXP2d2-rPAP1-luciferase reporter construct was co-transfected to follow STAT3 activation. Transfected cells were stimulated overnight with a serial dilution of leptin as indicated. Luciferase reporter activity (CPS, counts per second) is plotted as a function of the leptin concentration.

Panel B: Effect of cysteine mutations on leptin binding. Transfections were as in panel A. Cells were incubated with leptin-SEAP, with or without excess unlabeled leptin, for two hours. After four successive washing steps, bound alkaline phosphatase activity was measured using the CSPD substrate. Bars represent mean values of triplicate measurements.

Figure 4:
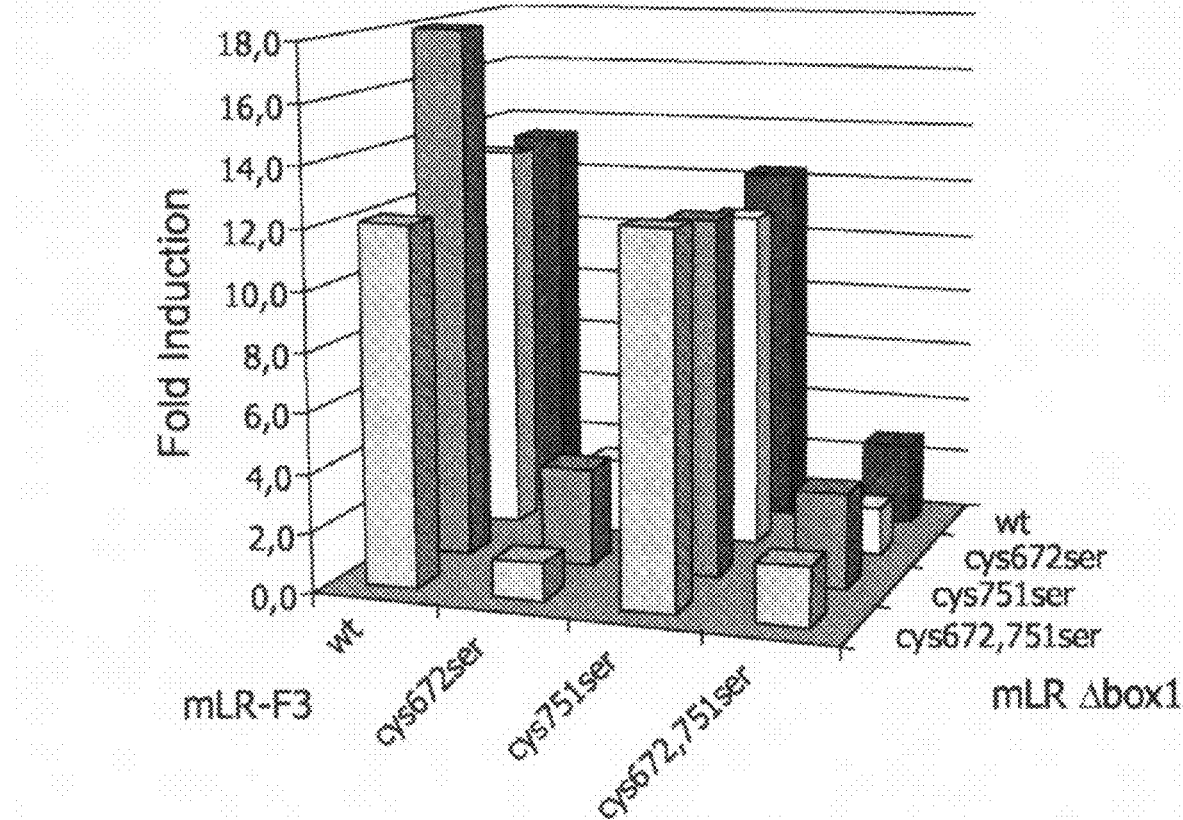

FIG. 4: Effect of cysteine mutations on complementation signaling: Hek293T cells were transiently co-transfected with plasmids encoding receptors mLR-F3 and mLR Δbox1, and cysteine mutants thereof. STAT3 activation was measured using the rPAP1-luciferase reporter after an overnight stimulation with 500 ng/ml leptin. Results are plotted as fold inductions, i.e., luciferase counts of stimulated cells, divided by those of the untreated cells.

Figure 5:
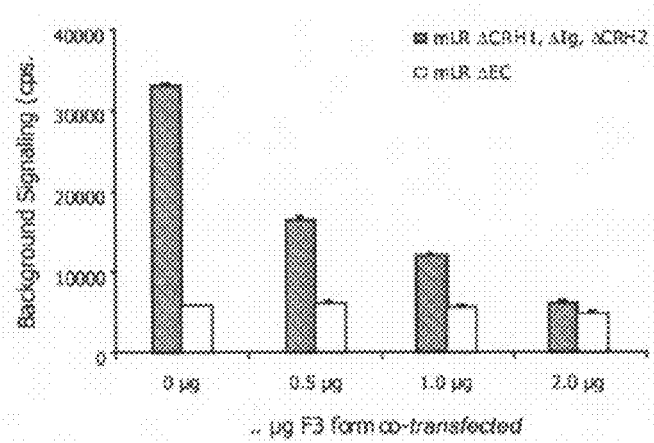

FIG. 5: Ligand-independent signaling by mLR deletion variants: 1 μg plasmid encoding the deletion variants mLR ΔCRH1, ΔIg, ΔCRH2 and mLR ΔEC were transfected alone or with increasing amounts (as indicated) of cDNA encoding their F3 counterpart. Differences in quantities transfected DNA were adjusted with empty pMET7 vector. Four days later, luciferase activity was measured as described above. Bars shown represent mean luciferase values and S.D. values of triplicate measurements.

Figure 6:
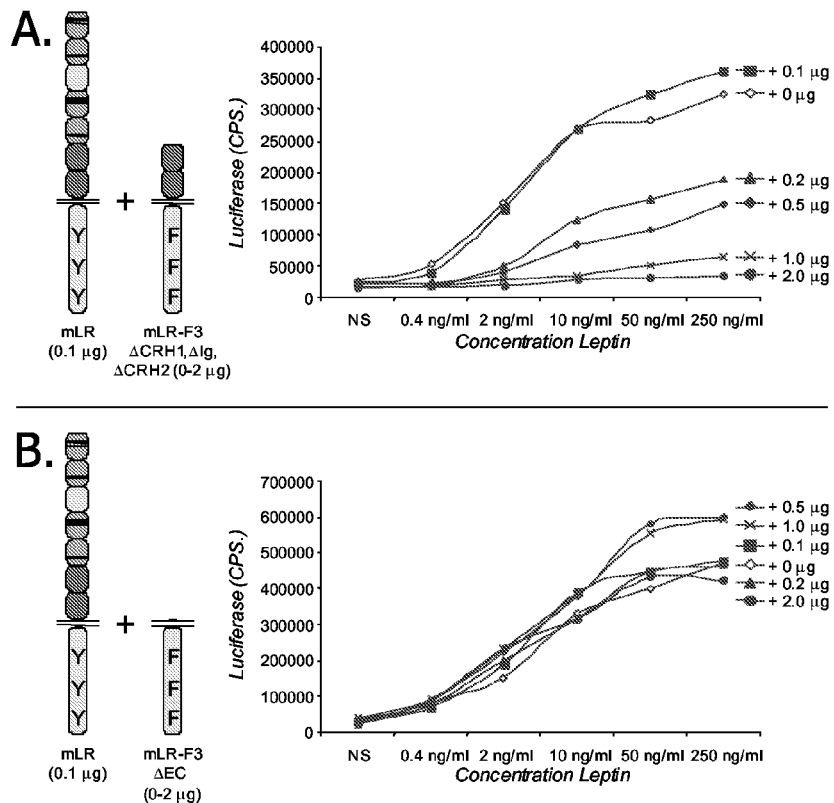

FIG. 6: Inhibition of LR signaling by truncated mutants: 0.1 μg plasmid encoding the mLR ΔCRH1 was co-transfected with different amounts of (A) mLR-F3 ΔCRH1, ΔIg, ΔCRH2 and (B) V5-mLR-F3 ΔEC as indicated. Differences in quantities of transfected DNA were adjusted with empty pMET7 vector. The rPAP1-luciferase reporter construct was also transfected to measure STAT3 activation. Cells were stimulated overnight with a serial dilution of leptin as indicated. Luciferase measurements were performed in triplicate as described above, and plotted as functions of the leptin concentrations.

Figure 7:
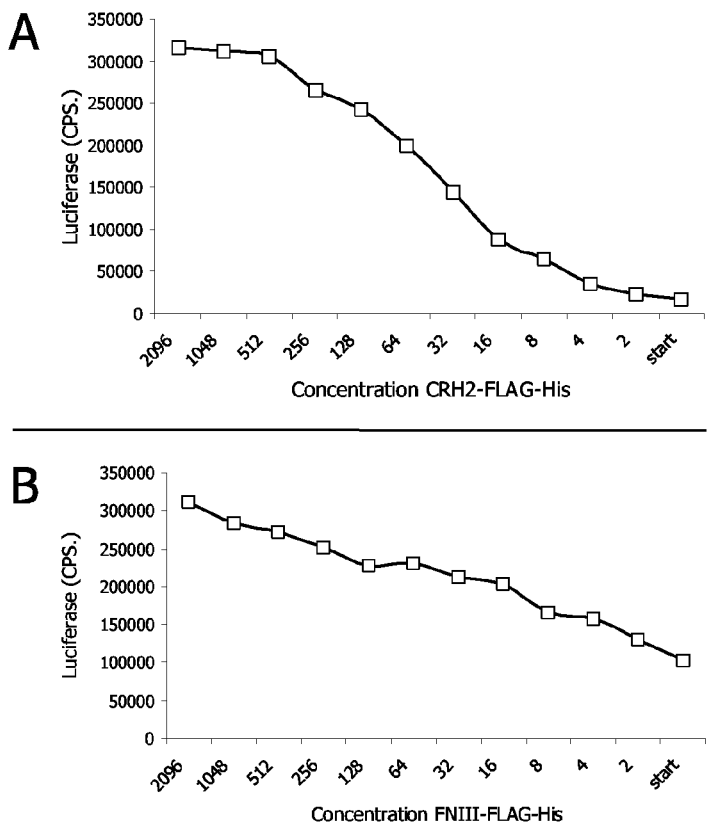

FIG. 7: Inhibition of LR signaling by LR domains: Hek293T cells were transiently transfected with plasmid encoding the wild-type mLR along with the rPAP1-luciferase reporter. After three days, cells were stimulated with 20 ng/ml leptin in the presence of a serial dilution (as indicated) CRH2-FLAG-His (panel A) or FNIII-FLAG-His protein (panel B). Luciferase measurements were as described above.

Figure 8:
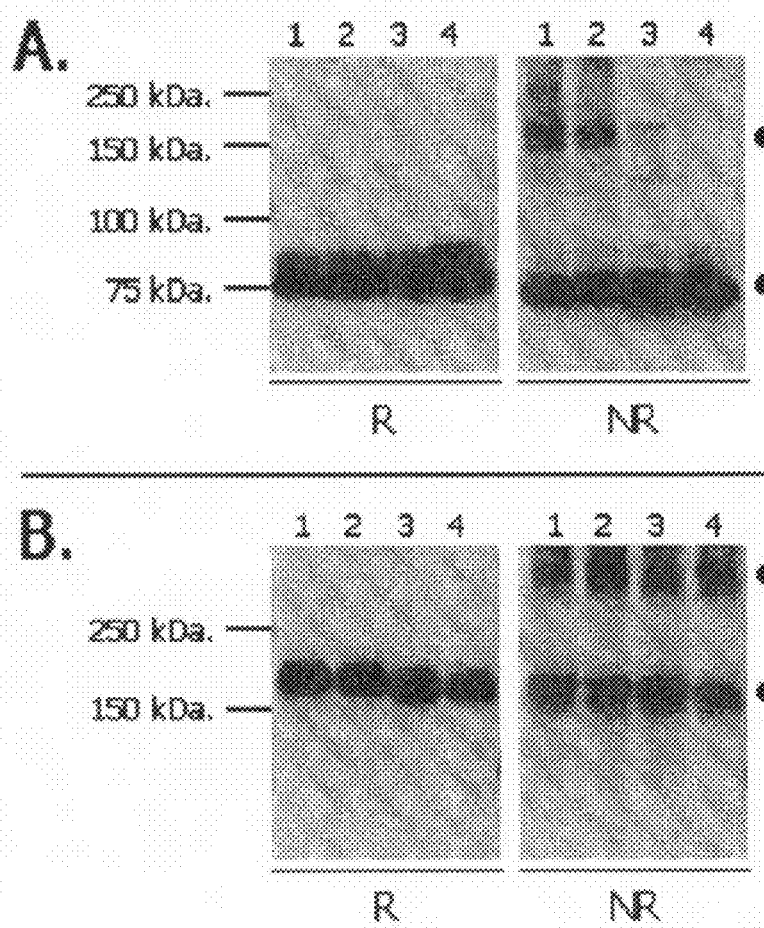

FIG. 8: Effect of mutation of cys672 and cys751 on disulphide linkage on the cellular membrane:

Panel A: Plasmids encoding (1) mLR ΔCRH1, ΔIg, ΔCRH2; (2) mLR ΔCRH1, ΔIg, ΔCRH2 cys672ser; (3) mLR ΔCRH1, ΔIg, ΔCRH2 cys751ser; (4) mLR ΔCRH1, ΔIg, ΔCRH2 cys672,751ser were transiently transfected in COS-1 cells. Transfected cells were lyzed in a reducing (R) or non-reducing (NR) loading buffer. Lysates were loaded on a SDS-PAGE gel, blotted to a nitro-cellulose membrane and subjected to Western blot with an anti-FLAG antibody.

Panel B: Cysteine mutants of the full length receptor—(1) mLR; (2) mLR cys672ser; (3) mLR cys751ser; (4) mLR cys672,751ser—were analyzed as described in panel A. ●●: dimers; ●: monomers.

FIG. 9: Clustering of CRH2 in solution:

Panel A: Plasmid pMET7 CRH2-FLAG-His was transiently transfected in COS-1 cells. Supernatant was subjected to Western blot analysis with an anti-FLAG antibody under reducing (R) and non-reducing (NR) conditions.

Panel B: Proteins CRH2-FLAG-His and CRH2-SEAP-FLAG were tested in the co-precipitation assay as described in FIG. 2. Bars shown represent mean values and S.D. values of triplicate measurements.

Panel C: The effect of co-expression was tested in the same experiment. Hek293T cells were transfected individually with plasmids encoding CRH2-FLAG-His, CRH2-SEAP-FLAG, or empty vector. The next day, cells were resuspended and equal amounts of cells expressing CRH2-FLAG-His and CRH2-SEAP-FLAG (filled bars), or cells transfected with CRH2-SEAP-FLAG and empty vector (open bars) were mixed. As a positive control, cells were transfected with a combination of FLAG-His and SEAP-FLAG fusion, or SEAP-FLAG and empty vector (see panel B). These transfected cells were also resuspended but not mixed. Two days later, the formation of oligomers was determined by subjecting supernatants of cell mixtures to co-precipitation with the metal affinity resin. Co-precipitated alkaline phosphatase activity was measured in triplicate as described above.

FIG. 10: Ligand-independent signaling by mLR deletion variants: Several mLR deletion variants (as indicated) were expressed in Hek293T cells along with the rPAP1-luciferase reporter. Four days later, luciferase activity was measured as described above. Bars shown represent mean luciferase values and S.D. values of triplicate measurements.

Figure 11:
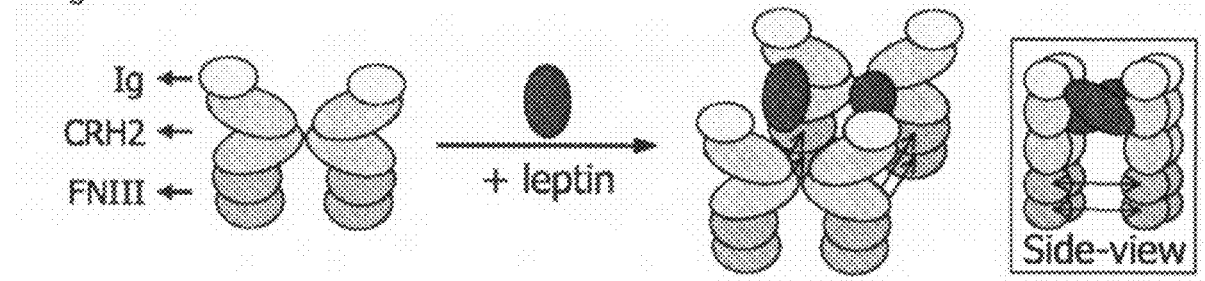

FIG. 11: Model for LR activation: For reasons of clarity, the membrane distal CRH1 domain was not included in the model. Arrows indicate covalent interactions between the FNIII domains. For abbreviations, see text.

Figure 12:
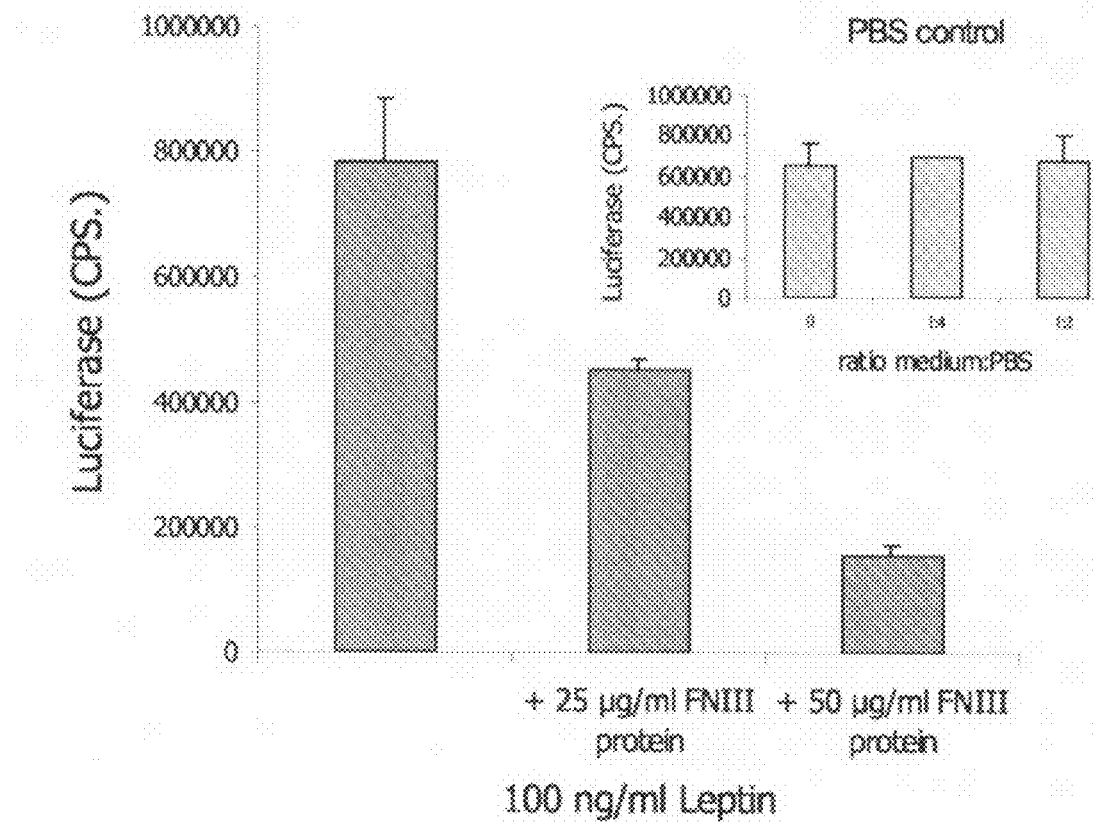

FIG. 12: inhibition by the soluble FNIII domain: A functional leptin receptor was activated by addition of 100 ng leptin per ml. Soluble FNIII domain was added as indicated and the activity of the receptor was measured by the luciferase activity as described above.

Figure 13:
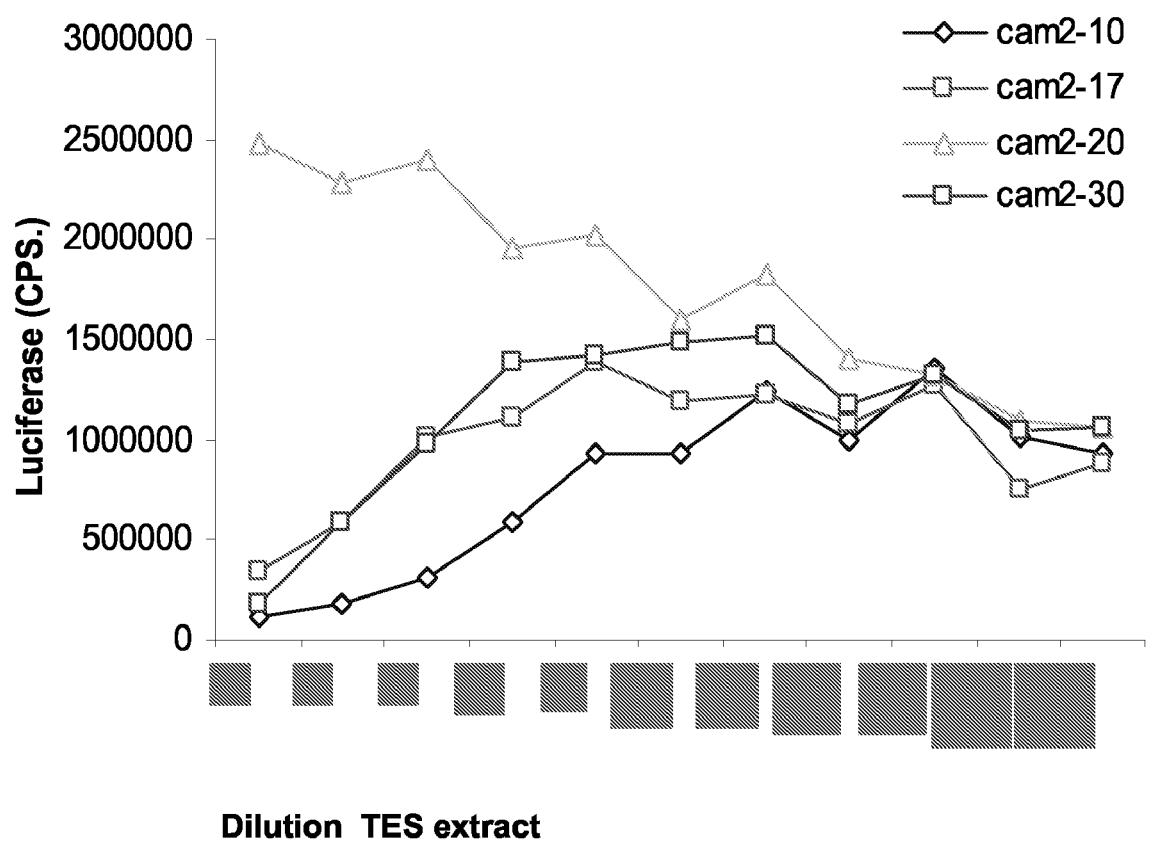

FIG. 13: Inhibition of leptin signaling by nanobodies: Hek293T cells transfected with the leptin receptor and the STAT3 responsive rPAP1-luciferase construct were stimulated with 20 ng/ml leptin. Cells were challenged by a serial dilution of neutralizing antibodies. Cam2-10: Ig-domain binding nanobody; cam2-17: CRH2 domain binding antibody; cam2-20 non-neutralizing leptin receptor binding antibody; cam2-30: FNIII domain binding antibody.

Figure 14:
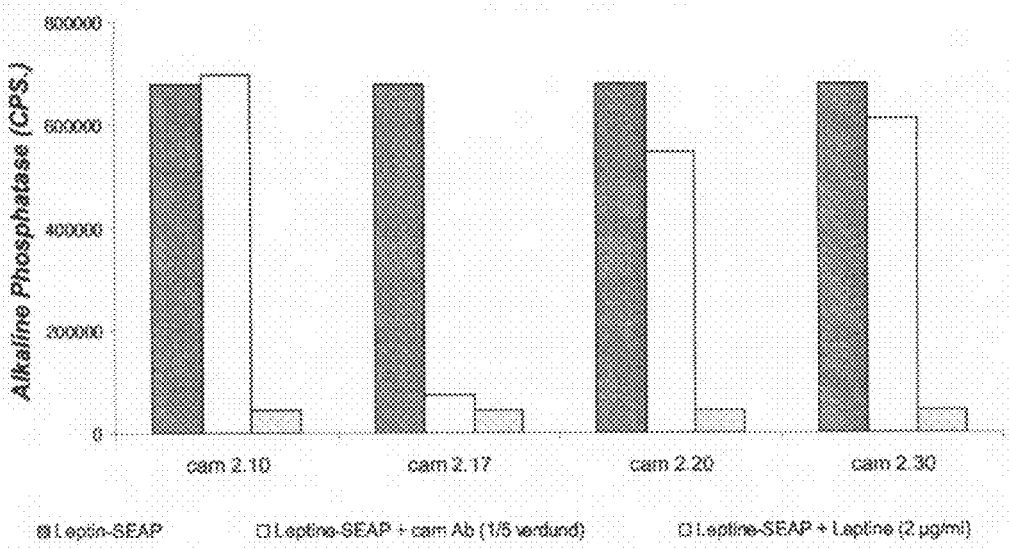

FIG. 14: Effect of the nanobodies on leptin binding to the receptor: Hek293T cells transfected with the leptin receptor. After 48 hours, the transfected cells were incubated with leptin-SEAP and a nanobody as indicated. An overload non-labeled leptin was used to check the specificity of the leptin-SEAP binding. After washing, the alkaline phosphatase activity was determined. Nanobody nomenclature as in FIG. 13.

Figure 15:
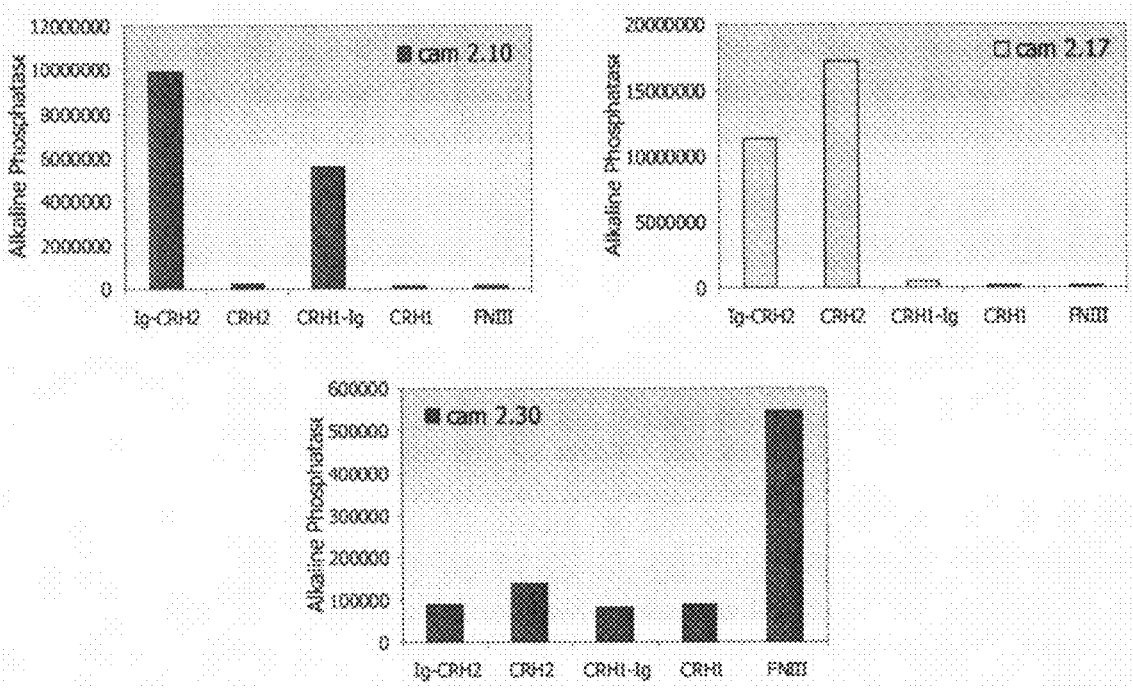

FIG. 15: Determination of the binding specificity of the nanobodies: His tagged nanobodies cam2-10, cam2-17 and cam2-30 (nomenclature as in FIG. 13) were fixed on anti-His coated maxi-sorp plates. SEAP coupled subdomains of the leptin receptor were bound to the plates and, after washing, the alkaline phosphatase activity was determined.

DETAILED DESCRIPTION OF THE INVENTION

Examples

Materials and Methods to the Examples

Vectors

Receptor deletion variants mLR ΔCRH1, and mLR ΔCRH1, ΔIg (and the F3 variants thereof, wherein all three cytosolic tyrosines are replaced by phenylalanine residues) have been constructed using a mutagenesis strategy (Zabeau et al., 2004). In brief, a Xho I site was introduced immediately following the signal-peptide encoding sequence. A second Xho I site was inserted following the sequence coding for the membrane distal CRH1 domain, or for the Ig-like domain. Resulting vectors were Xho I digested and circularized. Deletion variant mLR ΔCRH1,ΔIg,ΔCRH2 was made by PCR amplification with oligonucleotides 5'-GCG CTCGAGTCAAAGTTCCTATGAGAGGGCC-3' (with XhoI site) (SEQ ID NO:4) and 5'-CGCCGCAGCCGAAC-GACCGA-3' (50 bp downstream Kpn I site) (SEQ ID NO:5). The resulting amplicon was Xho I-Kpn I digested and ligated into the opened pMET7 mLR ΔCRH1, ΔIg vector. The vector pMET7 V5-mLR ΔEC encodes a LR variant in which the extracellular domain is replaced by the sequence encoding the V5 epitope. LR transmembrane and cytoplasmic domains were amplified with the forward primer 5'-GCG CTCGAGGTGGTAAGCCTATCCCTAACCCTCTCCT CGGTCTCGATTCTACG TTCACCAAAGATGCTATC-GAC-3' (with XhoI site, and V5 epitope sequence) (SEQ ID NO:6), and reverse primer 5'-CGCCGCAGCCGAACGAC-CGA-3' (SEQ ID NO:7). Also here, after Xho I-Kpn I digestion, the amplicon was inserted into the opened pMET7 mLR ΔCRH1,ΔIg vector.

Generation of the signaling-deficient LR mutants mLR-F3 and mLR Δbox1 (with two proline to serine mutations in the box 1 motif) has been described previously (Zabeau et al., 2004).

In the full-length receptor and in the deletion variants, the myc tag was replaced by the sequence coding for the FLAG tag. Therefore, the LR sequence between nucleotides 2161 to 2684 was amplified with oligonucleotides 5'-CCCTTGT-GAATTTTAACCTTACC-3' (50 bp upstream unique Dra III) (SEQ ID NO:8) and 5'-CGC TCTAGATTACTTATCGTCGTCATCCTTGTAATCCAC AGTTAAGTCACACATC-3' (with XbaI site, and FLAG epitope sequence) (SEQ ID NO:9). The amplicon was Dra III-Xba I digested and ligated in the appropriate expression vectors.

An expression vector wherein CRH2 is coupled to (i) the combined FLAG-His tag, or (ii) SEAP-FLAG, was constructed by inserting a Bgl II immediately following the sequence encoding the CRH2 domain in the pMET7 mLR ΔCRH1,ΔIg vector (mutagenesis primers with BglIIsite: 5'-GCTTGTCATGGATGTAAAGATCTCTATGAGAG GGCCTGAATTTTGG-3' (SEQ ID NO:10), and 5'-CCAAAATTCAGGCCCTCTCATAG AGATCTTTACATCCATGACAAGC-3' (SEQ ID NO:11). The resulting vector was cut with Bgl II and Xba I. (i) Oligonucleotides 5'-GATCTTAGATTACAAGGATGACGAC-GATAAGCACCACCACCACCACCACTAAT-3' (SEQ ID NO:12) and 5'-CTAGATTAGTGGTGGTGGTGGTGGT-GCTTATCGTCGTCAT CCTTGTAATCTAA-3' (SEQ ID NO:13), encode both FLAG and His tags, and ends are complementary to the Bgl II and Xba I sticky ends. Oligos were annealed and ligated into the opened vectors, resulting in FLAG-His tagged protein. (ii) Alternatively, oligonucleotides 5'-GCGGCG AGATCTCTATCATCCCAGTTGAGGAGGAGAACC-3' (with BglIIsite) (SEQ ID NO:14), and 5'-C CC TCTAGATTACTTATCGTCGTCATCCTTGTAATCAC CCGGG TGCGCGGCGTCG-3' (with XbaI site and FLAG sequence) (SEQ ID NO:15) were used to amplify the sequence encoding the secreted alkaline phosphatase (SEAP). The amplicon was digested with the enzymes Bgl II and Xba I, and ligated into the opened vector.

Expression vectors pMET7 mLR FNIII-FLAG-His and pMET7 mLR FNIII-SEAP-FLAG were constructed as follows: cDNA for FNIII domains was amplified using the primers 5'-GCGCTCGAGCCGTTCCTATGAGAGGGCCTG-3' (with XhoI) (SEQ ID NO:16) and 5'-CGCCGC AGATCTTCCCTGCGTCATTCTGCTGCTTGTCG-3' (with BglII) (SEQ ID NO:17). The CRH2 domain in pMET7 mLR CRH2-FLAG-His and pMET7 mLR CRH2-SEAP-FLAG was replaced by a cDNA fragment encoding the FNIII domains by a Xho I-Bgl II digestion of the amplicon and the appropriate vectors.

Free cysteine residues in the LR variants were mutated to serines. Primers used were 5'-CGAAAAATGACT-CACTCTCGAGTGTGAGGAGGTACG-3' (SEQ ID NO:18), and 5'-CGTACCTCCTCACACTCGAGAGT-GAGTCATTTTTCG-3' (SEQ ID NO:19) for cys672ser, and 5'-GCTTATCCCCTGAGCAGCTCGAGCGT- CATCCTTTCCTGG-3' (SEQ ID NO:20) and 5'CCAG-GAAAGGATGACGCTCGAGCTGCTCAGGG-GATAAGC-3' (SEQ ID NO:21) for the cys751ser mutation. The double mutant LR cys672,751ser was constructed by digestion of pMET7 mLR cys751ser with enzymes Dra III and Sac I. The resulting insert of 1507 bp was ligated in the Dra III-Sac I opened pMET7 mLR cys672ser.

Generation of the pXP2d2-rPAP1 (rat pancreatitis associated protein 1)-luciferase reporter was described before (Eyckerman et al., 2000). Activation of this reporter is dependent on STAT3. Over-expression of dominant-negative STAT3, but not of dominant-negative STAT1, completely blocks rPAP-luciferase reporter activation (Broekaert et al., 2002).

Nanobody Production

TG1 cells containing the nanobody clone were inoculated in 15 ml 2×TY medium supplemented with 100 µg/ml Ampicillin and 1% glucose. Cells were grown at 37° C. while shaking till $OD_{600}$ of 0.6-0.9 was reached. Nanobody expression was induced by adding IPTG to a final concentration of 1 mM. Induced cultures were further incubated overnight at 28° C. The next day, cells were harvested by centrifugation, resuspended in 200 µl TES buffer (200 mM Tris-HCl; pH 8.0, 0.5 mM EDTA, 500 mM sucrose), and incubated 20 minutes on ice. After addition of 300 µl TES/4 buffer (TES buffer diluted 1 over 4 with water), cells were kept another 30 minutes on ice. The extracts were finally cleared by centrifugation.

Cell Lines and Transfection Procedures

Hek293T and COS-1 cells were grown in DMEM medium with 4500 mg/l glucose supplemented with 10% fetal bovine serum (all from Invitrogen) in 10% $CO_2$ humidified atmosphere at 37° C. For transfection experiments, $4 \times 10^5$ cells per 10 cm² well were freshly seeded and cultured overnight. Hek293T and COS-1 cells were transfected overnight with standard calcium phosphate precipitation or polyethyleneimine procedures, respectively. One day after transfection, cells were washed with PBS-A and cultured overnight until further use (Western blot, co-precipitation, chemical cross-linking, reporter assay or leptin-SEAP binding).

Western Blot Analysis

Expression of LR or LR (deletion) mutants was monitored using Western blot analysis. Cells expressing the receptors were lyzed in 300 µl loading buffer and sonicated. Samples were loaded on a polyacrylamide gel, and blotted onto a nitrocellulose membrane. Proteins were revealed with a monoclonal antibody directed against the FLAG-tag (Sigma) and sheep anti-mouse horseradish peroxidase coupled secondary antibody (Amersham Bioscience).

Co-Precipitation

Hek293T cells were transiently transfected overnight with SEAP-FLAG and FLAG-His fusion protein vectors (or empty vector as a negative control). Three days after transfection, supernatants were collected and subjected to precipitation with the talon metal affinity resin (BD Bioscience). Fifty µl bed-volume resin per precipitation was washed three times with wash-buffer (50 mM $NaPO_4$, 300 mM NaCl, 0.5% NP40, pH 7.0). Supernatants were incubated with the resin for one hour at 4° C. After three washes with wash-buffer, precipitated complexes were eluted with an acidic elution buffer (50 mM sodium acetate, 300 mM NaCl, pH 5.0). Co-precipitated SEAP activity was measured using the chemiluminescent CSPD substrate (PhosphaLight, Tropix) in a TopCount Chemiluminescence Counter (Packard).

Reporter Assays

Two days after transfection, cells expressing different combinations of LR variants were resuspended with cell dissociation agent (Invitrogen) and seeded in a 96-well plate (Costar). Cells were stimulated overnight with leptin (R&D systems) as indicated, or were left un-stimulated. To test the neutralizing capacities of the nanobodies, cells were cultivated overnight with a serial dilution of nanobody-TES extract in combination with a fixed concentration of leptin (as indicated). Lysates were prepared (lysis buffer: 25 mM Tris, pH 7.8; 2 mM EDTA; 2 mM DTT; 10% glycerol; 1% Triton X-100), and 35 µl luciferase substrate buffer (20 mM Tricine; 1.07 mM $(MgCO_3)_4Mg(OH)_2.5H_2O$; 2.67 mM $MgSO_4.7H_2O$; 0.1 mM EDTA; 33.3 mM DDT; 270 µM Coenzyme A; 470 µM Luciferin; 530 µM ATP; final pH 7.8) was added per 50 µl lysate. Light emission was measured for five seconds in a TopCount Chemiluminescence Counter (Packard).

Leptin-SEAP Binding

Cell surface expression of wild-type LR or LR mutants was measured using a binding assay with a mouse leptin-SEAP chimeric protein. Two days after transfection, cells were washed (wash buffer: DMEM, 0.1% $NaN_3$, 20 mM Hepes pH 7.0, 0.01% Tween 20) and incubated for 90 minutes at room temperature with a 1/50 dilution of a COS-1 conditioned medium containing the leptin-SEAP chimera (final concentration: ±10 ng/ml). To test the effect of the nanobodies on binding, transfected cells were incubated with leptin-SEAP and a 1 over 5 dilution of the TES extracts. After three successive washing steps, cells were lyzed (lysis buffer: 1% TritonX-100, 10 mM Tris-HCl pH 7.4). Endogenous phosphatases in the lysates were inactivated (65° C., 30 minutes), and secreted alkaline phosphatase activity was measured as described above.

Production and Purification of LR Domains

The LR subdomain-SEAP fusion proteins were produced as follows: $2.5 \times 10^6$ COS-1 cells were seeded in 9 cm petri dishes and transfected overnight with plasmids encoding the SEAP fusion proteins. Cells were washed twice with PBS-A and cultured for five more days in medium supplemented with 1% serum. Supernatant was collected and stored until further use.

For the production of the proteins CRH2-FLAG-His or FNIII-FLAG-His $2.5 \times 10^7$ COS-1 cells were used in 625 cm² culture dishes. Five days after transfection, supernatants were collected and loaded on a 1 ml anti-FLAG M2 affinity column (Sigma) at a flow rate of 0.5 ml/minute. Column was washed with 50 ml washing buffer (150 mM NaCl; 20 mM Tris-HCl, pH 7.5; 5% glycerol; and 0.1% NP-40). Proteins were eluted with FLAG peptide (250 µg/ml in washing buffer). Positive fractions were collected, four times dialyzed against 5 liters PBS-A, and concentrated ten-fold with Vivaspin 15R concentrators, with a molecular mass cut-off of 5000 Da (Sartorius).

Example 1

Leptin Receptors Exist as Preformed Disulphide-Linked Oligomers on the Cell Surface A series of murine leptin receptor (mLR) deletion variants lacking extra-cellular sub-domains was generated as shown in FIG. 1. All variants were expressed in COS-1 cells and analyzed under reducing (β-mercapto-ethanol) or non-reducing conditions. As shown in FIG. 1, all deletion variants, except the one lacking the complete extra-cellular domain (mLR ΔEC), formed ligand-independent oligomers on the cellular surface. In all cases, monomers were observed under reducing conditions, indicating that disulphide bridges between the FNIII domains, and possibly also in other sub-domains, are involved in LR dimerization.

Example 2

Spontaneous Aggregation of FNIII Domains in Solution: Role of Disulphide Linkage We next analyzed the ligand-independent clustering of the FNIII domains in more detail. Constructs were generated to produce secreted forms of the FNIII domains, either as a FLAG-His-, or as a SEAP-FLAG-tagged protein. When FNIII-FLAG-His was expressed in COS-1 cells and analyzed under non-reducing conditions, di-, tri- and even higher order clusters were observed (FIG. 2, panel A). This clustering is independent of protein concentration since transfection with smaller amounts of expression vector gave the same clustering pattern. To confirm this FNIII-clustering, we set up a His/SEAP co-precipitation experiment. In this assay, FNIII-SEAP-FLAG proteins were co-expressed with FNIII-FLAG-His, or with empty vector as a negative control. Supernatants were analyzed in a precipitation experiment with a $Ni^{2+}$ affinity resin. Co-precipitated SEAP activity reflects interaction between the proteins. FIG. 2, panel B clearly confirms homotypic interaction of the FNIII domain.

The two mLR FNIII domains each contain a single free cysteine residue at positions 672 and 751, respectively (Haniu et al., 1998). Both residues were mutated to serines (cys672ser and cys751ser) in the soluble FNIII-FLAG-His construct. As shown in FIG. 2, panel C, both single mutations only slightly altered disulphide complex formation. In contrast, the double mutant (cys672,751ser) appeared in a monomeric form under non-reducing conditions, indicating that both cysteines are involved in the observed disulphide bonding.

Example 3

Conserved Cysteines in the FNIII Domain are Essential for LR Activation

To examine the role of the FNIII cys672 and cys751 residues in activation of the LR, we next analyzed the effect of cys to ser mutations in the membrane-bound wild-type LR long isoform. Single and double mutants were tested for their signaling capacity using a STAT3-dependent reporter assay in Hek293T cells. Results are shown in panel A of FIG. 3. Mutation cys672ser showed clear reduction on the activation of the rPAP1-luciferase reporter, while mLR cys751ser had signaling capacities comparable to the wild-type receptor. Combined mutation resulted in a receptor almost completely devoid of biological activity. As shown in FIG. 3, panel B, cell surface expression of all mutant receptors was comparable to the wild-type LR.

We next evaluated signaling using a complementation assay (Zabeau et al:, 2004). Cys to ser mutations were introduced in the signaling-deficient receptor mutants mLR-F3 (without functional STAT3 recruitment site) and mLR Δbox1 (unable to activate cytoplasmic associated JAK kinases). Different combinations of these receptors were transiently transfected in Hek293T cells, along with the rPAP1-luciferase reporter to follow STAT3 activation (FIG. 4). Data illustrate that mutation of cysteine on position 672 on itself in the mLR-F3 mutant is sufficient to completely block signaling.

Since this mutant is needed for activation of the JAK kinases in our complementation set-up, this indicates that cys672 is strictly necessary for JAK activation. Mutation of cysteine 751 had no major effect on signaling.

Example 4

The FNIII Domains Induce Ligand-Independent Signaling

We observed spontaneous, ligand-independent STAT3-dependent signaling in cells expressing mLR ΔCRH1, ΔIg, ΔCRH2 when compared to cells expressing a LR variant in which the complete extracellular domain is replaced by the V5-tag (FIG. 5). To test whether homotypic FNIII-FNIII interaction was responsible for this ligand-independent signaling, we analyzed the effect of co-expression of signaling-deficient mLR-F3 deletion variants. mLR ΔCRH1, ΔIg, ΔCRH2 and mLR ΔEC and an increasing amount of vector as indicated encoding their F3 counterpart were transiently co-transfected in Hek293T cells (FIG. 5). Clearly, leptin-independent activation of the mLR ΔCRH1, ΔIg, ΔCRH2 variant was reduced to the background levels observed for mLR ΔEC. It is of note that differences in ligand-independent activity could not simply be explained by differences in expression levels of the different LR deletion variants, as measured by Western blot analysis (see also FIG. 1). Together, these data lend further support to the role of (spatially correct) FNIII domain clustering for JAK activation and subsequent STAT3-dependent signaling. These data also rule out an important role of the trans-membrane domain in this process.

Example 5

Inhibition of LR Signaling by Homotypic FNIII-FNIII Interaction

Previous experiments showed that the FNIII domains, and cysteine residues therein, play a crucial role in LR activation. We next questioned whether preventing homotypic FNIII-FNIII interaction could inhibit leptin receptor signaling. In a first approach, we evaluated the effect of two STAT3-signaling-deficient F3 mutant receptors on wild-type LR signaling: mLR-F3 ΔCRH1, ΔIg, ΔCRH2 (with only the FNIII domains) and mLR-F3 ΔEC (wherein the complete extracellular domain was replaced by the V5-epitope). A vector encoding the wild-type mLR was co-transfected with increasing amounts of vector encoding the mLR-F3 variants (FIG. 6) and STAT3-dependent reporter activity was measured. Results clearly showed that only the LR-F3 variant with the FNIII domains could inhibit LR signaling. Since the FNIII domains cannot bind leptin themselves, these data implied that the mLR-F3 ΔCRH1, ΔIg, ΔCRH2 mutant is recruited in the complex only via FNIII-dependent receptor-receptor interactions.

In a second approach, we used soluble LR domains to inhibit signaling. Proteins CRH2-FLAG-His and FNIII-FLAG-His were expressed in COS-1 cells and affinity purified with an anti-FLAG antibody. Hek293T cells were transfected with the wild-type receptor and stimulated overnight with 20 ng/ml leptin in the presence of a serial dilution (as indicated) of the purified proteins. Results in FIG. 7 demonstrate clear inhibition of leptin-dependent signaling in both cases. Inhibition by CRH2-FLAG-His can obviously be explained by competition for binding of the ligand. FNIII-FLAG-His, lacking any affinity for leptin, can only block signaling by binding to the FNIII domains of membrane-bound receptors and thereby obstructing the formation of an active receptor complex. Both experimental set ups further point to the crucial role of the FNIII domains in the LR activation.

Example 6

Role of FNIII Cysteines in Disulphide-Dependent LR Oligomerization on the Cell Surface As with the soluble FNIII domains, combined mutation of residues cys672 and cys751 in LR ΔCRH1, ΔIg, ΔCRH2 completely abolished disulphide linkage on the cell surface (FIG. 8, panel A). The single cys751ser mutant receptor still showed dimerization, although to a lesser extent when compared to mLR wild-type and cys672ser. In strong contrast to this truncated receptor, mutation of cys672 and cys751 appeared to have no effect at all on disulphide bridging of the full-length receptor (panel B). This suggests that the free FNIII cysteine residues are not critical for the ligand-independent disulphide linkage of the wild-type receptor.

Example 7

The Ligand Binding CRH2 Domain Clustering in Solution

Since the FNIII domains appear not to be involved in leptin-independent clustering of the receptor, we next focused on the ligand-binding CRH2 domain. Like FNIII, this domain was expressed either as a FLAG-His tagged or as a SEAP-FLAG fusion protein. Western blot analysis showed that CRH2-FLAG-His was expressed as an oligomeric complex, which, similar to the FNIII domains, was sensitive to reduction (FIG. 8, panel A). This homotypic CRH2-CRH2 interaction was confirmed using a co-precipitation experiment as described for the FNIII domains (FIG. 9, panel B). This assay also allowed us to test whether the CRH2-CRH2 clustering occurs during biosynthesis. FIG. 9, panel C, clearly shows that co-precipitation was strictly dependent on co-expression of both tagged CRH2-proteins in the same cell.

Example 8

The CRH2 Domain Prevents Spontaneous FNIII-FNIII Clustering

Since both FNIII and CRH2 domains show homotypic clustering, we next questioned whether the CRH2-CRH2 interaction influences the spontaneous receptor activation elicited by FNIII domain interactions. Different LR deletion variants were transiently transfected and leptin-independent signaling was measured by co-transfection of the rPAP1-luciferase reporter (FIG. 10). Results clearly indicate that the presence of CRH2 (alone, or in combination with Ig and CRH1) reduces FNIII-mediated signaling to background level. These data strongly suggest that homotypic CRH2-CRH2 interactions keep the FNIII domains spatially apart so that no spontaneous JAK activation and hence signaling can occur. A model of the receptor cluster is shown in FIG. 11.

Example 9

Addition of Soluble FNIII Domain Inhibits the Activity of the Leptin Receptor

Cells carrying a functional leptin receptor were activated by 100 ng/ml leptin and the activity of the receptor was measured using the rPAP1-luciferase assay as described above. Soluble FNIII domain (SEQ ID NO:3) was added to the medium, and the decrease in luciferase activity was measured. The results are shown in FIG. 12. The leptin-induced activity can clearly be inhibited by addition of the non-leptin binding FNIII domains.

Example 10

Anti-FNIII Nanobody Inhibits Leptin Signaling but not Leptin Binding to the Receptor Camels were immunized with the extracellular part of the leptin receptor. Lymphocytes were isolated from the camel blood and used as source of mRNA. Using this RNA as template, VHH sequences were cloned by PCR and inserted in the pax51 vector, allowing phage display and selection of the antibodies. For all the domains (CRH2, Ig and FNIII), binding antibodies have been isolated. One representative antibody for each domain was used for further research. (Cam2-10: Ig-domain binding nanobody; cam2-17: CRH2 domain binding antibody; cam2-20 non-neutralizing leptin receptor binding antibody; cam2-30: FNIII domain binding antibody.) Those nanobodies were produced in *E. coli*. A serial dilution of periplasmic TES extract of the bacteria was added to FEK293T cells, transfected with the leptin receptor and a rPAP1-luciferase reporter construct. The results are summarized in FIG. 13. All antibodies (including the anti-FNIII antibody), except the non-neutralizing one, show an inhibitory effect on leptin signaling at the higher concentration. As a control, to check the leptin receptor specificity, the effect of the antibodies on LIF signaling was tested, but no inhibitory effect on the LIF receptor could be noticed.

To prove that the inhibitory effect was not due to an inhibition of the leptin binding, HEK293T cells transfected with leptin receptor were incubated with leptin-SEAP, with or without addition of antibody. As a control for the specificity of the binding, non-labeled leptin was used to compete with the leptin-SEAP binding. Cells were washed and the alkaline phosphatase activity was measured. The results are shown in FIG. 14. Only the CRH2 antibody interfered with the leptin binding. Indeed, Fong et al. (1998) demonstrated already that the CHR domain is necessary for leptin binding. Therefore, binding of an antibody to this domain is supposed to impair leptin binding. However, it is clear that for the anti-FNIII nanobody as well as for the anti-Ig nanobody, the binding and inhibitory effect of leptin signaling is not caused by an inhibition of the leptin binding to the receptor.

Example 11

The Binding of Cam2-30 is Specific for the FNIII Domain

To test the specificity of the different antibodies, the Ig-CRH2, CRH2, CRH1-Ig, CRH1 and FNIII domains of the extracellular part of the receptor (see FIG. 1) were fused to SEAP and expressed in Cos 1 cells. Maxi-sorb plates were coated with anti-HIS antibodies, and the different his tagged nanobodies were bound on the plates. Supernatant of the domain expressing Cos 1 cells was added to the wells. After washing, SEAP alkaline phosphatase activity was tested. The results are summarized in FIG. 15. It is clear that all antibodies show a strict domain-specific reaction, and that cam2-30 only binds to the FNIII domain. Therefore, the inhibiting effect of this antibody is clearly caused by its binding to the FNIII domain, and the antibody can inhibit leptin-induced signaling, even when leptin is bound to the receptor.

REFERENCES

Baile C. A., Della-Fera M. A., Martin R. J. 2000. Regulation of metabolism and body fat mass by leptin. Annu. Rev. Nutr. 20:105-27.

Broekaert D., Eyckerman S., Lavens D., Verhee A., Waelput W., Vandekerckhove J., Tavernier J. 2002. Comparison of leptin- and interleukin-6-regulated expression of the rPAP gene family: evidence for differential co-regulatory signals. Eur. Cytokine Netw. 13:78-85.

Campfield L. A., Smith F. J., Guisez Y., Devos R., Burn P. 1995. Recombinant mouse OB protein: evidence for a peripheral signal linking adiposity and central neural networks. Science 269:546-9.

Chehab F. F., Qiu J., Mounzih K., Ewart-Toland A., Ogus S. 2002. Leptin and reproduction. Nutr. Rev. 60:39-46.

Chen H., Charlat O., Tartaglia L. A., et al. 1996. Evidence that the diabetes gene encodes the leptin receptor: identification of a mutation in the leptin receptor gene in db/db mice. Cell 84:491-5.

Cioffi J. A., Shafer A. W., Zupancic T. J., Smith-Gbur J., Mikhail A., Platika D., Snodgrass H. R. 1996. Novel B219/OB receptor isoforms: possible role of leptin in hematopoiesis and reproduction. Nat. Med. 2:585-9.

Clement K., Vaisse C., Lahlou N., et al. 1998. A mutation in the human leptin receptor gene causes obesity and pituitary dysfunction. Nature 392:398-401.

Dyer C. J., Simmons J. M., Matteri R. L., Keisler D. H. 1997. Leptin receptor mRNA is expressed in ewe anterior pituitary and adipose tissues and is differentially expressed in hypothalamic regions of well-fed and feed-restricted ewes. Domest. Anim. Endocrinol. 14:119-28.

Eyckerman S., Broekaert D., Verhee A., Vandekerckhove J., Tavernier J. 2000. Identification of the Y985 and Y1077 motifs as SOCS3 recruitment sites in the murine leptin receptor. FEBS Lett. 486:33-7.

Fantuzzi G., Faggioni R. 2000. Leptin in the regulation of immunity, inflammation, and hematopoiesis. J. Leukoc. Biol. 68:437-46.

Fei H., Okano H. J., Li C., Lee G. H., Zhao C., Darnell R., Friedman J. M. 1997. Anatomic localization of alternatively spliced leptin receptors (Ob-R) in mouse brain and other tissues. Proc. Natl. Acad. Sci. U. S. A. 94:7001-5.

Fong T. M., Huang R. R., Tota M. R., Mao C., Smith T., Varnerin J., Karpitskiy V. V., Krause J. E., Van der Ploeg L. H. 1998. Localization of leptin binding domain in the leptin receptor. Mol. Pharmacol. 53:234-40.

Halaas J. L., Gajiwala K. S., Maffei M., Cohen S. L., Chait B. T., Rabinowitz D., Lallone R. L., Burley S. K., Friedman J. M. 1995. Weight-reducing effects of the plasma protein encoded by the obese gene. Science 269:543-6.

Haniu M., Arakawa T., Bures E. J., Young Y., Hui J. O., Rohde M. F., Welcher A. A., Horan T. 1998. Human leptin receptor. Determination of disulfide structure and N-glycosylation sites of the extracellular domain. J. Biol. Chem. 273: 28691-9.

Hoggard N., Mercer J. G., Rayner D. V., Moar K., Trayhurn P., Williams L. M. 1997. Localization of leptin receptor mRNA splice variants in murine peripheral tissues by RT-PCR and in situ hybridization. Biochem. Biophys. Res. Commun. 232:383-7.

Lee G. H., Proenca R., Montez J. M., Carroll K. M., Darvishzadeh J. G., Lee J. I., Friedman J. M. 1996. Abnormal splicing of the leptin receptor in diabetic mice. Nature 379:632-5.

Madej T., Boguski M. S., Bryant S. H. 1995. Threading analysis suggests that the obese gene product may be a helical cytokine. FEBS Lett. 373:13-8.

Matarese G., La Cava A., Sanna V., Lord G. M., Lechler R. I., Fontana S., Zappacosta S. 2002. Balancing susceptibility to infection and autoimmunity: a role for leptin? Trends Immunol. 2002 23:182-7.

Mercer J. G., Hoggard N., Williams L. M., Lawrence C. B., Hannah L. T., Trayhurn P. 1996. Localization of leptin receptor mRNA and the long form splice variant (Ob-Rb) in mouse hypothalamus and adjacent brain regions by in situ hybridization. FEBS Lett. 387:113-6.

Montague C. T., Farooqi I. S., Whitehead J. P., et al. 1997. Congenital leptin deficiency is associated with severe early-onset obesity in humans. Nature 387:903-8.

Pelleymounter M. A., Cullen M. J., Baker M. B., Hecht R., Winters D., Boone T., Collins F. 1995. Effects of the obese gene product on body weight regulation in ob/ob mice. Science 269:540-3.

Schwartz M. W., Seeley R. J., Campfield L. A., Burn P., Baskin D. G. 1996. Identification of targets of leptin action in rat hypothalamus. J. Clin. Invest. 98:1101-6.

Tartaglia L. A., Dembski M., Weng X., et al. 1995. Identification and expression cloning of a leptin receptor, OB-R. Cell 83:1263-71.

Tartaglia L. A. 1997. The leptin receptor. J. Biol. Chem. 272:6093-6.

Zabeau L., Defeau D., Van der Heyden J., Iserentant H., Vandekerckhove J., Tavernier J. 2004. Functional analysis of leptin receptor activation using a Janus kinase/signal transducer and activator of transcription complementation assay. Mol. Endocrinol. 18:150-61.

```
                           SEQUENCE LISTING

<160> NUMBER OF SEQ ID NOS: 21

<210> SEQ ID NO 1
<211> LENGTH: 97
<212> TYPE: PRT
<213> ORGANISM: Artificial Sequence
<220> FEATURE:
<223> OTHER INFORMATION: FNIII domain of human leptin receptor

<400> SEQUENCE: 1

Pro Met Arg Gly Pro Glu Phe Trp Arg Lys Met Asp Gly Asp Val Thr
1               5                   10                  15

Lys Lys Glu Arg Asn Val Thr Leu Leu Trp Lys Pro Leu Thr Lys Asn
            20                  25                  30

Asp Ser Leu Cys Ser Val Arg Arg Tyr Val Val Lys His Arg Thr Ala
        35                  40                  45

His Asn Gly Thr Trp Ser Glu Asp Val Gly Asn Arg Thr Asn Leu Thr
    50                  55                  60

Phe Leu Trp Thr Glu Pro Ala His Thr Val Thr Val Leu Ala Val Asn
65                  70                  75                  80

Ser Leu Gly Ala Ser Leu Val Asn Phe Asn Leu Thr Phe Ser Trp Pro
                85                  90                  95

Met

<210> SEQ ID NO 2
<211> LENGTH: 94
<212> TYPE: PRT
<213> ORGANISM: Artificial Sequence
<220> FEATURE:
<223> OTHER INFORMATION: FNIII domain of human leptin receptor

<400> SEQUENCE: 2

Ser Lys Val Ser Ala Val Glu Ser Leu Ser Ala Tyr Pro Leu Ser Ser
1               5                   10                  15

Ser Cys Val Ile Leu Ser Trp Thr Leu Ser Pro Asp Asp Tyr Ser Leu
            20                  25                  30

Leu Tyr Leu Val Ile Glu Trp Lys Ile Leu Asn Glu Asp Asp Gly Met
        35                  40                  45

Lys Trp Leu Arg Ile Pro Ser Asn Val Lys Lys Phe Tyr Ile His Asp
    50                  55                  60

Asn Phe Ile Pro Ile Glu Lys Tyr Gln Phe Ser Leu Tyr Pro Val Phe
```

```
                65                  70                  75                  80
Met Glu Gly Val Gly Lys Pro Lys Ile Ile Asn Gly Phe Thr
                    85                  90
```

<210> SEQ ID NO 3
<211> LENGTH: 191
<212> TYPE: PRT
<213> ORGANISM: Artificial Sequence
<220> FEATURE:
<223> OTHER INFORMATION: FNIII domain of human leptin receptor

<400> SEQUENCE: 3

```
Pro Met Arg Gly Pro Glu Phe Trp Arg Lys Met Asp Gly Asp Val Thr
1               5                   10                  15
Lys Lys Glu Arg Asn Val Thr Leu Leu Trp Lys Pro Leu Thr Lys Asn
                20                  25                  30
Asp Ser Leu Cys Ser Val Arg Arg Tyr Val Val Lys His Arg Thr Ala
            35                  40                  45
His Asn Gly Thr Trp Ser Glu Asp Val Gly Asn Arg Thr Asn Leu Thr
        50                  55                  60
Phe Leu Trp Thr Glu Pro Ala His Thr Val Thr Val Leu Ala Val Asn
65                  70                  75                  80
Ser Leu Gly Ala Ser Leu Val Asn Phe Asn Leu Thr Phe Ser Trp Pro
                85                  90                  95
Met Ser Lys Val Ser Ala Val Glu Ser Leu Ser Ala Tyr Pro Leu Ser
                100                 105                 110
Ser Ser Cys Val Ile Leu Ser Trp Thr Leu Ser Pro Asp Asp Tyr Ser
            115                 120                 125
Leu Leu Tyr Leu Val Ile Glu Trp Lys Ile Leu Asn Glu Asp Asp Gly
        130                 135                 140
Met Lys Trp Leu Arg Ile Pro Ser Asn Val Lys Lys Phe Tyr Ile His
145                 150                 155                 160
Asp Asn Phe Ile Pro Ile Glu Lys Tyr Gln Phe Ser Leu Tyr Pro Val
                165                 170                 175
Phe Met Glu Gly Val Gly Lys Pro Lys Ile Ile Asn Gly Phe Thr
                180                 185                 190
```

<210> SEQ ID NO 4
<211> LENGTH: 31
<212> TYPE: DNA
<213> ORGANISM: Artificial Sequence
<220> FEATURE:
<223> OTHER INFORMATION: oligonucleotide used for PCR amplification
<220> FEATURE:
<221> NAME/KEY: misc_feature
<222> LOCATION: (4)..(9)
<223> OTHER INFORMATION: Xho I site

<400> SEQUENCE: 4
gcgctcgagt caaagttcct atgagagggc c                              31

<210> SEQ ID NO 5
<211> LENGTH: 20
<212> TYPE: DNA
<213> ORGANISM: Artificial Sequence
<220> FEATURE:
<223> OTHER INFORMATION: oligonucleotide used for PCR amplification (50
      bp downstream Kpn I site)

<400> SEQUENCE: 5
cgccgcagcc gaacgaccga                                           20

<210> SEQ ID NO 6
<211> LENGTH: 74
<212> TYPE: DNA
<213> ORGANISM: Artificial Sequence
<220> FEATURE:
<223> OTHER INFORMATION: forward primer
<220> FEATURE:
<221> NAME/KEY: misc_feature
<222> LOCATION: (4)..(9)
<223> OTHER INFORMATION: Xho I site
<220> FEATURE:
<221> NAME/KEY: misc_feature
<222> LOCATION: (12)..(50)
<223> OTHER INFORMATION: V5 epitope sequence

<400> SEQUENCE: 6
gcgctcgagg tggtaagcct atccctaacc ctctcctcgg tctcgattct acgttcacca      60
aagatgctat cgac      74

<210> SEQ ID NO 7
<211> LENGTH: 20
<212> TYPE: DNA
<213> ORGANISM: Artificial Sequence
<220> FEATURE:
<223> OTHER INFORMATION: reverse primer

<400> SEQUENCE: 7
cgccgcagcc gaacgaccga      20

<210> SEQ ID NO 8
<211> LENGTH: 23
<212> TYPE: DNA
<213> ORGANISM: Artificial Sequence
<220> FEATURE:
<223> OTHER INFORMATION: oligonucleotide primer (50 bp upstream unique
      Dra III)

<400> SEQUENCE: 8
cccttgtgaa ttttaacctt acc      23

<210> SEQ ID NO 9
<211> LENGTH: 55
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (4)..(9)
<223> OTHER INFORMATION: Xba I site
<220> FEATURE:
<221> NAME/KEY: misc_feature
<222> LOCATION: (10)..(34)
<223> OTHER INFORMATION: FLAG epitope sequence

<400> SEQUENCE: 9
cgctctagat tacttatcgt cgtcatcctt gtaatccaca gttaagtcac acatc      55

<210> SEQ ID NO 10
<211> LENGTH: 46
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (18)..(23)
<223> OTHER INFORMATION: BgI II site

<400> SEQUENCE: 10
gcttgtcatg gatgtaaaga tctctatgag agggcctgaa ttttgg                    46

<210> SEQ ID NO 11
<211> LENGTH: 46
<212> TYPE: DNA
<213> ORGANISM: Artificial Sequence
<220> FEATURE:
<223> OTHER INFORMATION: mutagenesis primer
<220> FEATURE:
<221> NAME/KEY: misc_feature
<222> LOCATION: (24)..(29)
<223> OTHER INFORMATION: Bgl II site

<400> SEQUENCE: 11
ccaaaattca ggccctctca tagagatctt tacatccatg acaagc                    46

<210> SEQ ID NO 12
<211> LENGTH: 53
<212> TYPE: DNA
<213> ORGANISM: Artificial Sequence
<220> FEATURE:
<223> OTHER INFORMATION: oligonucleotide

<400> SEQUENCE: 12
gatcttagat tacaaggatg acgacgataa gcaccaccac caccaccact aat            53

<210> SEQ ID NO 13
<211> LENGTH: 53
<212> TYPE: DNA
<213> ORGANISM: Artificial Sequence
<220> FEATURE:
<223> OTHER INFORMATION: oligonucleotide

<400> SEQUENCE: 13
ctagattagt ggtggtggtg gtggtgctta tcgtcgtcat ccttgtaatc taa            53

<210> SEQ ID NO 14
<211> LENGTH: 39
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (7)..(12)
<223> OTHER INFORMATION: Bgl II site

<400> SEQUENCE: 14
gcggcgagat ctctatcatc ccagttgagg aggagaacc                            39

<210> SEQ ID NO 15
<211> LENGTH: 56
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (5)..(10)
<223> OTHER INFORMATION: Xba I site
<220> FEATURE:
<221> NAME/KEY: misc_feature
<222> LOCATION: (11)..(35)
<223> OTHER INFORMATION: FLAG sequence

<400> SEQUENCE: 15

```
cgcctctaga ttacttatcg tcgtcatcct tgtaatcacc cgggtgcgcg gcgtcg          56
```

<210> SEQ ID NO 16
<211> LENGTH: 30
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (4)..(9)
<223> OTHER INFORMATION: Xho I site

<400> SEQUENCE: 16

```
gcgctcgagc cgttcctatg agagggcctg                                      30
```

<210> SEQ ID NO 17
<211> LENGTH: 38
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (7)..(12)
<223> OTHER INFORMATION: Bgl II site

<400> SEQUENCE: 17

```
cgccgcagat cttccctgcg tcattctgct gcttgtcg                             38
```

<210> SEQ ID NO 18
<211> LENGTH: 36
<212> TYPE: DNA
<213> ORGANISM: Artificial Sequence
<220> FEATURE:
<223> OTHER INFORMATION: primer for cys672ser mutation

<400> SEQUENCE: 18

```
cgaaaaatga ctcactctcg agtgtgagga ggtacg                               36
```

<210> SEQ ID NO 19
<211> LENGTH: 36
<212> TYPE: DNA
<213> ORGANISM: Artificial Sequence
<220> FEATURE:
<223> OTHER INFORMATION: primer for cys672ser mutation

<400> SEQUENCE: 19

```
cgtacctcct cacactcgag agtgagtcat ttttcg                               36
```

<210> SEQ ID NO 20
<211> LENGTH: 39
<212> TYPE: DNA
<213> ORGANISM: Artificial Sequence
<220> FEATURE:
<223> OTHER INFORMATION: primer for cys751ser mutation

<400> SEQUENCE: 20

```
gcttatcccc tgagcagctc gagcgtcatc ctttcctgg                            39
```

<210> SEQ ID NO 21
<211> LENGTH: 39
<212> TYPE: DNA

```
<213> ORGANISM: Artificial Sequence
<220> FEATURE:
<223> OTHER INFORMATION: primer for cys751ser mutation

<400> SEQUENCE: 21
ccaggaaagg atgacgctcg agctgctcag gggataagc                              39
```

The invention claimed is:

1. A method of inhibiting leptin-induced signaling, said method comprising:

blocking tetramerization of the leptin receptor with an anti-fibronectin III domain antibody, wherein the blocking of tetramerization of the leptin receptor with the anti-fibronectin III domain antibody inhibits leptin induced signalling.

2. The method according to claim 1, wherein said inhibition occurs in the presence of leptin bound to leptin-binding domain of leptin receptor.

3. A method of inhibiting leptin-induced signaling of a leptin receptor, the method comprising inhibiting leptin-induced signaling with an anti-fibronectin III domain antibody, in the presence of leptin binding to said leptin receptor, whereby said anti-fibronectin III domain antibody blocks tetramerization of the leptin receptor.

* * * * *

UNITED STATES PATENT AND TRADEMARK OFFICE
CERTIFICATE OF CORRECTION

PATENT NO. : 7,575,878 B2
APPLICATION NO. : 11/791264
DATED : August 18, 2009
INVENTOR(S) : Jan Tavernier and Lennart Zabeau It is certified that error appears in the above-identified patent and that said Letters Patent is hereby corrected as shown below:

On the title page:
In ITEM (54) and
COLUMN 1, LINE 1-3, change "METHODS OF INHIBITING LEPTIN-INDUCED SIGNALING WITH FIBRONECTIN III DOMAIN ANTIBODIES" to --FIBRONECTIN III DOMAIN AS LEPTIN RECEPTOR ANTAGONISTS--

In the specification:
COLUMN 6, LINE 61, change "XhoI" to --Xho I--
COLUMN 7, LINE 4, change "XhoI" to --Xho I--
COLUMN 7, LINE 20, change "XbaI" to --Xba I--
COLUMN 7, LINE 28, change "BglIIsite:" to --Bgl II site:--
COLUMN 7, LINE 44, change "BglIIsite)" to --Bgl II site)--
COLUMN 7, LINE 46, change "XbaI" to --Xba I--
COLUMN 7, LINE 55, change "XhoI)" to --Xho I)--
COLUMN 7, LINE 57, change "BglII)" to --Bgl II)--

Signed and Sealed this
Sixteenth Day of April, 2013

Teresa Stanek Rea
*Acting Director of the United States Patent and Trademark Office*

CERTIFICATE OF CORRECTION (continued)

U.S. Pat. No. 7,575,878 B2

COLUMN 25, LINE 9, after
"<400> SEQUENCE: 21
ccaggaaagg atgacgctcg agctgctcag gggataagc                    39"

insert

--<210> 22

<211> 5

<212> PRT

<213> Artificial Sequence

<220>
<221> misc_feature

<222> (2)..(4)

<223> oligopeptide motif characteristic of C-terminal sub-domains in cytokine receptors, Xaa is any amino acid <400> 22
Trp Ser Xaa Trp Ser
1               5--